United States Patent
Libbus et al.

(10) Patent No.: US 8,805,494 B2
(45) Date of Patent: Aug. 12, 2014

(54) SYSTEM AND METHOD TO DELIVER THERAPY IN PRESENCE OF ANOTHER THERAPY

(71) Applicant: Cardiac Pacemakers, Inc., St. Paul, MN (US)

(72) Inventors: Imad Libbus, St. Paul, MN (US); Andrew P. Kramer, Marine on St. Croix, MN (US); William J. Linder, Golden Valley, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/954,342

(22) Filed: Jul. 30, 2013

(65) Prior Publication Data

US 2013/0317561 A1 Nov. 28, 2013

Related U.S. Application Data

(60) Continuation of application No. 13/397,115, filed on Feb. 15, 2012, now Pat. No. 8,504,149, which is a division of application No. 12/148,843, filed on Apr. 23, 2008, now Pat. No. 8,131,359, which is a division of application No. 11/125,503, filed on May 10, 2005, now Pat. No. 7,493,161.

(51) Int. Cl.
*A61N 1/05* (2006.01)
(52) U.S. Cl.
USPC .................................................. 607/4; 607/2
(58) Field of Classification Search
None
See application file for complete search history.

(56) References Cited

U.S. PATENT DOCUMENTS

| | | | |
|---|---|---|---|
| 3,421,511 A | 1/1969 | Schwartz et al. |
| 3,650,277 A | 3/1972 | Sjostrand et al. |
| 4,201,219 A | 5/1980 | Bozal Gonzalez |
| 4,592,359 A | 6/1986 | Galbraith |
| 4,702,254 A | 10/1987 | Zabara |
| 4,763,646 A | 8/1988 | Lekholm |

(Continued)

FOREIGN PATENT DOCUMENTS

| | | |
|---|---|---|
| EP | 0547734 A2 | 6/1993 |
| EP | 0688578 A1 | 12/1995 |

(Continued)

OTHER PUBLICATIONS

"U.S. Appl. No. 11/125,503, Notice of Allowance mailed Jan. 4, 2008", 8 pgs.

(Continued)

*Primary Examiner* — Brian T Gedeon
(74) *Attorney, Agent, or Firm* — Schwegman Lundberg & Woessner, P.A.

(57) ABSTRACT

Various aspects relate to a method. In various embodiments, a therapy of a first therapy type is delivered, and it is identified whether a therapy of a second therapy type is present to affect the therapy of the first therapy type. Delivery of the therapy is controlled based on the presence of the therapy of the second therapy type. Some embodiments deliver the therapy of the first type using one set of parameters in the presence of a therapy of a second type, and deliver the therapy of the first type using another set of parameters when the therapy of the second type is not present. In various embodiments, one of the therapy types includes a cardiac rhythm management therapy, and the other includes a neural stimulation therapy. Other aspects and embodiments are provided herein.

20 Claims, 10 Drawing Sheets

(56) References Cited

U.S. PATENT DOCUMENTS

| | | |
|---|---|---|
| 4,770,177 A | 9/1988 | Schroeppel |
| 4,791,931 A | 12/1988 | Slate |
| 4,880,005 A | 11/1989 | Pless et al. |
| 4,936,304 A | 6/1990 | Kresh et al. |
| 4,960,129 A | 10/1990 | dePaola et al. |
| 5,014,698 A | 5/1991 | Cohen |
| 5,052,388 A | 10/1991 | Sivula et al. |
| 5,111,815 A | 5/1992 | Mower |
| 5,199,428 A | 4/1993 | Obel et al. |
| 5,203,326 A | 4/1993 | Collins |
| 5,224,475 A | 7/1993 | Berg et al. |
| 5,243,980 A | 9/1993 | Mehra |
| 5,318,592 A | 6/1994 | Schaldach |
| 5,330,507 A | 7/1994 | Schwartz |
| 5,334,221 A | 8/1994 | Bardy |
| 5,356,425 A | 10/1994 | Bardy et al. |
| 5,403,351 A | 4/1995 | Saksena |
| 5,411,531 A | 5/1995 | Hill et al. |
| 5,437,285 A | 8/1995 | Verrier et al. |
| 5,507,784 A | 4/1996 | Hill et al. |
| 5,522,854 A | 6/1996 | Ideker et al. |
| 5,540,730 A | 7/1996 | Terry, Jr. et al. |
| 5,562,711 A | 10/1996 | Yerich et al. |
| 5,578,061 A | 11/1996 | Stroetmann et al. |
| 5,626,621 A | 5/1997 | Skoglund et al. |
| 5,658,318 A | 8/1997 | Stroetmann et al. |
| 5,662,689 A | 9/1997 | Elsberry et al. |
| 5,690,681 A | 11/1997 | Geddes et al. |
| 5,700,282 A | 12/1997 | Zabara |
| 5,731,848 A | 3/1998 | Patel et al. |
| 5,792,187 A | 8/1998 | Adams |
| 5,817,131 A | 10/1998 | Elsberry et al. |
| 5,893,881 A | 4/1999 | Elsberry et al. |
| 5,916,239 A | 6/1999 | Geddes et al. |
| 5,928,272 A | 7/1999 | Adkins et al. |
| 6,006,134 A | 12/1999 | Hill et al. |
| 6,018,682 A | 1/2000 | Rise |
| 6,058,331 A | 5/2000 | King |
| 6,073,048 A | 6/2000 | Kieval et al. |
| 6,104,956 A | 8/2000 | Naritoku et al. |
| 6,119,043 A | 9/2000 | Hsu et al. |
| 6,134,470 A | 10/2000 | Hartlaub |
| 6,178,349 B1 | 1/2001 | Kieval |
| 6,205,359 B1 | 3/2001 | Boveja |
| 6,240,314 B1 | 5/2001 | Plicchi et al. |
| 6,292,695 B1 | 9/2001 | Webster, Jr. et al. |
| 6,304,772 B1 | 10/2001 | Taha et al. |
| 6,337,997 B1 | 1/2002 | Rise |
| 6,341,236 B1 | 1/2002 | Osorio et al. |
| 6,349,233 B1 | 2/2002 | Adams |
| 6,356,788 B2 | 3/2002 | Boveja |
| 6,363,278 B1 | 3/2002 | Stahmann et al. |
| 6,371,922 B1 | 4/2002 | Baumann et al. |
| 6,400,982 B2 | 6/2002 | Sweeney et al. |
| 6,415,183 B1 | 7/2002 | Scheiner et al. |
| 6,421,557 B1 | 7/2002 | Meyer |
| 6,438,423 B1 | 8/2002 | Rezai et al. |
| 6,449,507 B1 | 9/2002 | Hill et al. |
| 6,466,822 B1 | 10/2002 | Pless |
| 6,473,644 B1 | 10/2002 | Terry, Jr. et al. |
| 6,477,404 B1 | 11/2002 | Yonce et al. |
| 6,477,418 B2 | 11/2002 | Plicchi et al. |
| 6,487,446 B1 | 11/2002 | Hill et al. |
| 6,487,450 B1 | 11/2002 | Chen et al. |
| 6,493,585 B2 | 12/2002 | Plicchi et al. |
| 6,511,500 B1 | 1/2003 | Rahme |
| 6,522,926 B1 | 2/2003 | Kieval et al. |
| 6,532,388 B1 | 3/2003 | Hill et al. |
| 6,542,774 B2 | 4/2003 | Hill et al. |
| 6,564,096 B2 | 5/2003 | Mest |
| 6,587,727 B2 | 7/2003 | Osorio et al. |
| 6,597,954 B1 | 7/2003 | Pless et al. |
| 6,600,954 B2 | 7/2003 | Cohen et al. |
| 6,610,713 B2 | 8/2003 | Tracey |
| 6,611,713 B2 | 8/2003 | Schauerte |
| 6,622,041 B2 | 9/2003 | Terry, Jr. et al. |
| 6,628,987 B1 | 9/2003 | Hill et al. |
| 6,658,287 B1 | 12/2003 | Litt et al. |
| 6,668,191 B1 | 12/2003 | Boveja |
| 6,671,556 B2 | 12/2003 | Osorio et al. |
| 6,684,105 B2 | 1/2004 | Cohen et al. |
| 6,690,974 B2 | 2/2004 | Archer et al. |
| 6,735,471 B2 | 5/2004 | Hill et al. |
| 6,788,975 B1 | 9/2004 | Whitehurst et al. |
| 6,810,285 B2 | 10/2004 | Pless et al. |
| 6,920,357 B2 | 7/2005 | Osorio et al. |
| 6,922,585 B2 | 7/2005 | Zhou et al. |
| 6,928,324 B2 | 8/2005 | Park et al. |
| 6,934,583 B2 | 8/2005 | Weinberg et al. |
| 6,937,896 B1 | 8/2005 | Kroll |
| 6,965,797 B2 | 11/2005 | Pastore et al. |
| 7,025,730 B2 | 4/2006 | Cho et al. |
| 7,039,466 B1 | 5/2006 | Harrison et al. |
| 7,069,070 B2 | 6/2006 | Carlson et al. |
| 7,123,961 B1 | 10/2006 | Kroll et al. |
| 7,123,967 B2 | 10/2006 | Weinberg |
| 7,139,607 B1 | 11/2006 | Shelchuk |
| 7,155,278 B2 | 12/2006 | King et al. |
| 7,158,832 B2 | 1/2007 | Kieval et al. |
| 7,260,431 B2 | 8/2007 | Libbus et al. |
| 7,277,761 B2 | 10/2007 | Shelchuk |
| 7,299,086 B2 | 11/2007 | McCabe et al. |
| 7,493,161 B2 | 2/2009 | Libbus et al. |
| 7,542,794 B1 | 6/2009 | Zhang et al. |
| 7,542,800 B2 | 6/2009 | Libbus et al. |
| 7,565,195 B1 | 7/2009 | Kroll et al. |
| 7,570,999 B2 | 8/2009 | Libbus et al. |
| 7,587,238 B2 | 9/2009 | Moffitt et al. |
| 7,657,312 B2 | 2/2010 | Pastore et al. |
| 7,660,628 B2 | 2/2010 | Libbus et al. |
| 7,665,195 B1 | 2/2010 | Vazquez-Perez |
| 7,769,450 B2 | 8/2010 | Libbus et al. |
| 7,840,271 B2 | 11/2010 | Kieval |
| 7,873,413 B2 | 1/2011 | McCabe et al. |
| 8,131,359 B2 | 3/2012 | Libbus et al. |
| 2001/0003799 A1 | 6/2001 | Boveja |
| 2001/0016759 A1 | 8/2001 | Kramer et al. |
| 2002/0016344 A1 | 2/2002 | Tracey |
| 2002/0016550 A1 | 2/2002 | Sweeney et al. |
| 2002/0026221 A1 | 2/2002 | Hill et al. |
| 2002/0026222 A1 | 2/2002 | Schauerte et al. |
| 2002/0035378 A1 | 3/2002 | Bardy et al. |
| 2002/0058877 A1 | 5/2002 | Baumann et al. |
| 2002/0072776 A1 | 6/2002 | Osorio et al. |
| 2002/0077670 A1 | 6/2002 | Archer et al. |
| 2002/0082661 A1 | 6/2002 | Plicchi et al. |
| 2002/0091415 A1 | 7/2002 | Lovett et al. |
| 2002/0107553 A1 | 8/2002 | Hill et al. |
| 2002/0116030 A1 | 8/2002 | Rezai |
| 2002/0120304 A1 | 8/2002 | Mest |
| 2002/0123769 A1 | 9/2002 | Panken et al. |
| 2002/0143369 A1 | 10/2002 | Hill et al. |
| 2002/0161410 A1 | 10/2002 | Kramer et al. |
| 2002/0165586 A1 | 11/2002 | Hill et al. |
| 2002/0169485 A1 | 11/2002 | Pless et al. |
| 2002/0183237 A1 | 12/2002 | Puskas |
| 2002/0188325 A1 | 12/2002 | Hill et al. |
| 2002/0188326 A1 | 12/2002 | Zheng et al. |
| 2002/0198570 A1 | 12/2002 | Puskas |
| 2003/0004549 A1 | 1/2003 | Hill et al. |
| 2003/0023279 A1 | 1/2003 | Spinelli et al. |
| 2003/0040774 A1 | 2/2003 | Terry, Jr. et al. |
| 2003/0045909 A1 | 3/2003 | Gross et al. |
| 2003/0045914 A1 | 3/2003 | Cohen et al. |
| 2003/0060848 A1 | 3/2003 | Keival et al. |
| 2003/0060857 A1 | 3/2003 | Perrson et al. |
| 2003/0060858 A1 | 3/2003 | Kieval et al. |
| 2003/0074039 A1 | 4/2003 | Puskas |
| 2003/0078623 A1 | 4/2003 | Weinberg et al. |
| 2003/0078629 A1 | 4/2003 | Chen |
| 2003/0100924 A1 | 5/2003 | Foreman et al. |
| 2003/0105493 A1 | 6/2003 | Salo |
| 2003/0149450 A1 | 8/2003 | Mayberg |
| 2003/0153953 A1 | 8/2003 | Park et al. |

(56) References Cited

U.S. PATENT DOCUMENTS

| | | |
|---|---|---|
| 2003/0181951 A1 | 9/2003 | Cates |
| 2003/0181958 A1 | 9/2003 | Dobak |
| 2003/0195578 A1 | 10/2003 | Perron et al. |
| 2003/0212440 A1 | 11/2003 | Boveja |
| 2003/0212445 A1 | 11/2003 | Weinberg |
| 2003/0216792 A1 | 11/2003 | Levin et al. |
| 2003/0229380 A1 | 12/2003 | Adams et al. |
| 2003/0236558 A1 | 12/2003 | Whitehurst et al. |
| 2004/0002635 A1 | 1/2004 | Hargrove et al. |
| 2004/0010303 A1 | 1/2004 | Bolea et al. |
| 2004/0015204 A1 | 1/2004 | Whitehurst et al. |
| 2004/0044377 A1 | 3/2004 | Larsson |
| 2004/0049120 A1 | 3/2004 | Cao et al. |
| 2004/0054381 A1 | 3/2004 | Pastore et al. |
| 2004/0082980 A1 | 4/2004 | Mouine et al. |
| 2004/0088009 A1 | 5/2004 | Degroot |
| 2004/0088015 A1 | 5/2004 | Casavant et al. |
| 2004/0102820 A1 | 5/2004 | Mouine et al. |
| 2004/0116970 A1 | 6/2004 | Girouard et al. |
| 2004/0133248 A1 | 7/2004 | Frei et al. |
| 2004/0138721 A1 | 7/2004 | Osorio et al. |
| 2004/0138724 A1 | 7/2004 | Sieracki et al. |
| 2004/0158295 A1 | 8/2004 | Dyjach et al. |
| 2004/0162594 A1 | 8/2004 | King |
| 2004/0172074 A1 | 9/2004 | Yoshihito |
| 2004/0172075 A1 | 9/2004 | Shafer et al. |
| 2004/0172089 A1 | 9/2004 | Whitehurst et al. |
| 2004/0172094 A1 | 9/2004 | Cohen et al. |
| 2004/0193231 A1 | 9/2004 | David et al. |
| 2004/0199210 A1 | 10/2004 | Shelchuk |
| 2004/0210261 A1 | 10/2004 | King et al. |
| 2004/0215289 A1 | 10/2004 | Fukui |
| 2004/0220621 A1 | 11/2004 | Zhou et al. |
| 2004/0254612 A1 | 12/2004 | Ezra et al. |
| 2005/0010263 A1 | 1/2005 | Schauerte |
| 2005/0015129 A1 | 1/2005 | Mische |
| 2005/0021092 A1 | 1/2005 | Yun et al. |
| 2005/0027321 A1 | 2/2005 | Ferek-Petric |
| 2005/0059897 A1 | 3/2005 | Snell et al. |
| 2005/0060001 A1 | 3/2005 | Singhal et al. |
| 2005/0065554 A1 | 3/2005 | KenKnight et al. |
| 2005/0065555 A1 | 3/2005 | Er |
| 2005/0065575 A1 | 3/2005 | Dobak |
| 2005/0075690 A1 | 4/2005 | Toy et al. |
| 2005/0075701 A1 | 4/2005 | Shafer |
| 2005/0085864 A1 | 4/2005 | Schulman et al. |
| 2005/0096705 A1 | 5/2005 | Pastore et al. |
| 2005/0107844 A1 | 5/2005 | Van Den Honert et al. |
| 2005/0143779 A1 | 6/2005 | Libbus |
| 2005/0143785 A1 | 6/2005 | Libbus |
| 2005/0143787 A1 | 6/2005 | Boveja et al. |
| 2005/0148896 A1 | 7/2005 | Siejko et al. |
| 2005/0149126 A1 | 7/2005 | Libbus |
| 2005/0149127 A1 | 7/2005 | Libbus |
| 2005/0149128 A1 | 7/2005 | Heil, Jr. et al. |
| 2005/0149129 A1 | 7/2005 | Libbus et al. |
| 2005/0149130 A1 | 7/2005 | Libbus |
| 2005/0149131 A1 | 7/2005 | Libbus et al. |
| 2005/0149132 A1 | 7/2005 | Libbus |
| 2005/0149133 A1 | 7/2005 | Libbus et al. |
| 2005/0149143 A1 | 7/2005 | Libbus et al. |
| 2005/0149148 A1 | 7/2005 | King |
| 2005/0149155 A1 | 7/2005 | Scheiner et al. |
| 2005/0149156 A1 | 7/2005 | Libbus et al. |
| 2005/0154418 A1 | 7/2005 | Kieval et al. |
| 2005/0182288 A1 | 8/2005 | Zabara |
| 2005/0182453 A1 | 8/2005 | Whitehurst et al. |
| 2005/0187584 A1 | 8/2005 | Denker et al. |
| 2005/0197600 A1 | 9/2005 | Schuler et al. |
| 2005/0197674 A1 | 9/2005 | McCabe et al. |
| 2005/0251216 A1 | 11/2005 | Hill et al. |
| 2005/0261741 A1 | 11/2005 | Libbus et al. |
| 2006/0004417 A1 | 1/2006 | Rossing et al. |
| 2006/0020297 A1 | 1/2006 | Gerber et al. |
| 2006/0052831 A1 | 3/2006 | Fukui |
| 2006/0079945 A1 | 4/2006 | Libbus |
| 2006/0095080 A1 | 5/2006 | Libbus et al. |
| 2006/0106429 A1 | 5/2006 | Libbus et al. |
| 2006/0116737 A1 | 6/2006 | Libbus |
| 2006/0122675 A1 | 6/2006 | Libbus et al. |
| 2006/0167497 A1 | 7/2006 | Armstrong et al. |
| 2006/0195038 A1 | 8/2006 | Carlson et al. |
| 2006/0206153 A1 | 9/2006 | Libbus et al. |
| 2006/0206154 A1 | 9/2006 | Moffitt et al. |
| 2006/0206158 A1 | 9/2006 | Wu et al. |
| 2006/0206159 A1 | 9/2006 | Moffitt et al. |
| 2006/0217772 A1 | 9/2006 | Libbus et al. |
| 2006/0224188 A1 | 10/2006 | Libbus et al. |
| 2006/0224202 A1 | 10/2006 | Moffitt et al. |
| 2006/0229677 A1 | 10/2006 | Moffitt et al. |
| 2006/0241699 A1 | 10/2006 | Libbus et al. |
| 2006/0241725 A1 | 10/2006 | Libbus |
| 2006/0253156 A1 | 11/2006 | Pastore et al. |
| 2006/0259083 A1 | 11/2006 | Libbus et al. |
| 2006/0271118 A1 | 11/2006 | Libbus et al. |
| 2007/0021790 A1 | 1/2007 | Kieval et al. |
| 2007/0021799 A1 | 1/2007 | Kieval et al. |
| 2007/0038261 A1 | 2/2007 | Kieval et al. |
| 2007/0142864 A1 | 6/2007 | Libbus et al. |
| 2007/0142871 A1 | 6/2007 | Libbus et al. |
| 2008/0015648 A1 | 1/2008 | Libbus et al. |
| 2008/0021504 A1 | 1/2008 | McCabe et al. |
| 2008/0167693 A1 | 7/2008 | Kieval et al. |
| 2008/0167694 A1 | 7/2008 | Bolea et al. |
| 2008/0200959 A1 | 8/2008 | Libbus et al. |
| 2008/0228238 A1 | 9/2008 | Libbus |
| 2009/0018596 A1 | 1/2009 | Kieval |
| 2009/0030484 A1 | 1/2009 | Chambers |
| 2009/0228060 A1 | 9/2009 | Libbus et al. |
| 2010/0121399 A1 | 5/2010 | McCabe et al. |
| 2010/0285196 A1 | 11/2010 | Moore et al. |
| 2011/0106199 A1 | 5/2011 | Mccabe et al. |
| 2011/0137360 A1 | 6/2011 | Ternes et al. |
| 2012/0150250 A1 | 6/2012 | Libbus |

FOREIGN PATENT DOCUMENTS

| | | |
|---|---|---|
| EP | 0709112 | 5/1996 |
| EP | 0721786 A2 | 7/1996 |
| EP | 1304135 A2 | 4/2003 |
| EP | 1421973 A2 | 5/2004 |
| EP | 1421973 A3 | 5/2004 |
| EP | 1426078 A1 | 6/2004 |
| EP | 1486232 A2 | 12/2004 |
| EP | 1541193 A1 | 6/2005 |
| JP | 8-52121 | 2/1996 |
| JP | 2004173791 A | 6/2004 |
| JP | 2004351122 A | 12/2004 |
| JP | 2005500863 A | 1/2005 |
| WO | WO-9216257 A1 | 10/1992 |
| WO | WO-9713550 A1 | 4/1997 |
| WO | WO-9904329 | 1/1999 |
| WO | WO-9965561 A1 | 12/1999 |
| WO | WO-0004950 A2 | 2/2000 |
| WO | WO-0226318 A1 | 4/2002 |
| WO | WO-0234327 A2 | 5/2002 |
| WO | WO-02085448 A2 | 10/2002 |
| WO | WO-02087694 A1 | 11/2002 |
| WO | WO-03011388 A2 | 2/2003 |
| WO | WO-03018108 A3 | 3/2003 |
| WO | WO-03020364 A2 | 3/2003 |
| WO | WO-03041559 A2 | 5/2003 |
| WO | WO-03076008 A1 | 9/2003 |
| WO | WO-03082080 A3 | 10/2003 |
| WO | WO-03099373 A2 | 12/2003 |
| WO | WO-03099377 A1 | 12/2003 |
| WO | WO-2004012814 A1 | 2/2004 |
| WO | WO-2004033036 A2 | 4/2004 |
| WO | WO-2004084990 A1 | 10/2004 |
| WO | WO-2004084993 A1 | 10/2004 |
| WO | WO-2004103455 A2 | 12/2004 |
| WO | WO-2004105870 A1 | 12/2004 |
| WO | WO-2004110549 A2 | 12/2004 |
| WO | WO-2004110550 A2 | 12/2004 |

(56) References Cited

FOREIGN PATENT DOCUMENTS

| WO | WO-2005018739 A1 | 3/2005 |
|---|---|---|
| WO | WO-2005042091 A1 | 5/2005 |
| WO | WO-2005063332 A1 | 7/2005 |
| WO | WO-2005065771 A1 | 7/2005 |
| WO | WO-2005113066 A1 | 12/2005 |
| WO | WO-2006031331 A1 | 3/2006 |
| WO | WO-2006044025 A1 | 4/2006 |
| WO | WO-2006055436 A1 | 5/2006 |
| WO | WO-2006107675 A1 | 10/2006 |
| WO | WO-2006121929 A1 | 11/2006 |
| WO | WO-2006127248 A1 | 11/2006 |
| WO | WO-2007078410 A1 | 7/2007 |
| WO | WO-2008063396 A1 | 5/2008 |
| WO | WO-2008144354 A1 | 11/2008 |
| WO | WO-2011071896 A1 | 6/2011 |
| WO | WO-2011088222 A1 | 7/2011 |

OTHER PUBLICATIONS

"U.S. Appl. No. 10/746,846, Final Office Action mailed Jan. 23, 2008", 18 pgs.

"U.S. Appl. No. 10/746,846, Final Office Action mailed Feb. 12, 2007", 17 pgs.

"U.S. Appl. No. 10/746,846, Non Final Office Action mailed Apr. 26, 2007", 18 pgs.

"U.S. Appl. No. 10/746,846, Non Final Office Action mailed Jul. 25, 2006", 15 pgs.

"U.S. Appl. No. 10/746,846, Response filed Apr. 17, 2007 to Final Office Action mailed Feb. 12, 2007", 16 pgs.

"U.S. Appl. No. 10/746,846, Response filed Jul. 7, 2006 to Restriction Requirement mailed Jun. 9, 2006", 13 pgs.

"U.S. Appl. No. 10/746,846, Response filed Oct. 26, 2007 to Non Final Office Action mailed Apr. 26, 2007", 11 pgs.

"U.S. Appl. No. 10/746,846, Response filed Nov. 9, 2006 to Non Final Office Action mailed Jul. 25, 2006", 17 pgs.

"U.S. Appl. No. 10/746,846, Restriction Requirement mailed Jun. 9, 2006", 7 pgs.

"U.S. Appl. No. 10/962,845, Appeal Brief mailed Sep. 26, 2007", 33 pgs.

"U.S. Appl. No. 10/962,845, Final Office Action mailed Jan. 26, 2007", 7 pgs.

"U.S. Appl. No. 10/962,845, Non Final Office Action mailed May 12, 2006", 10 pgs.

"U.S. Appl. No. 10/962,845, Preliminary Amendment filed Apr. 25, 2005", 11 pgs.

"U.S. Appl. No. 10/962,845, Response filed Oct. 12, 2006 to Non Final Office Action mailed May 12, 2006", 14 pgs.

"U.S. Appl. No. 11/099,141, Final Office Action mailed Oct. 22, 2007", 9 pgs.

"U.S. Appl. No. 11/099,141, Final Office Action mailed Nov. 7, 2008", 8 pgs.

"U.S. Appl. No. 11/099,141, Non-Final Office Action mailed May 6, 2008", 11 pgs.

"U.S. Appl. No. 11/099,141, Non-Final Office Action mailed May 18, 2007", 8 pgs.

"U.S. Appl. No. 11/099,141, Notice of Allowance mailed Jan. 28, 2009", 4 pgs.

"U.S. Appl. No. 11/099,141, Response filed Jan. 6, 2009 to Final Final Office Action mailed Nov. 7, 2008", 9 pgs.

"U.S. Appl. No. 11/099,141, Response filed Feb. 19, 2008 to Final Office Action mailed Oct. 22, 2007", 13 pgs.

"U.S. Appl. No. 11/099,141, Response filed Apr. 5, 2007 to Restriction Requirement mailed Mar. 6, 2007", 11 pgs.

"U.S. Appl. No. 11/099,141, Response filed Aug. 4, 2008 to Non Final Office Action mailed May 6, 2008", 10 pgs.

"U.S. Appl. No. 11/099,141, Response filed Aug. 20, 2007 to Non Final Office Action mailed May 18, 2007", 11 pgs.

"U.S. Appl. No. 11/099,141, Restriction Requirement mailed Mar. 6, 2007", 6 pgs.

"U.S. Appl. No. 11/125,503, Examiner Interview Summary mailed Oct. 18, 2007", 4 pgs.

"U.S. Appl. No. 11/125,503, Non-Final Office Action mailed Jun. 28, 2007", 8 pgs.

"U.S. Appl. No. 11/125,503, Notice of Allowance mailed Mar. 8, 2007", 8 pgs.

"U.S. Appl. No. 11/125,503, Response filed Oct. 29, 2007 to Non Final Office Action mailed Jun. 28, 2007", 21 pgs.

"U.S. Appl. No. 11/137,038, Appeal Brief mailed Jan. 18, 2010", 35 pgs.

"U.S. Appl. No. 11/137,038, Final Office Action mailed Aug. 14, 2009", 10 pgs.

"U.S. Appl. No. 11/137,038, Final Office Action mailed Aug. 29, 2008", FOAR, 10 pgs.

"U.S. Appl. No. 11/137,038, Non-Final Office Action mailed Feb. 5, 2008", OARN, 8 pgs.

"U.S. Appl. No. 11/312,178, Non-Final Office Action mailed May 14, 2008", 6 pgs.

"U.S. Appl. No. 11/312,178, Notice of Allowance mailed Apr. 3, 2009", 6 pgs.

"U.S. Appl. No. 11/312,178, Notice of Allowance mailed Nov. 14, 2008", 6 pgs.

"U.S. Appl. No. 11/312,178, Preliminary Amendment filed Mar. 14, 2006", 7 pgs.

"U.S. Appl. No. 11/312,178, Response filed Aug. 14, 2008 to Non Final Office Action mailed May 14, 2008", 14 pgs.

"U.S. Appl. No. 11/459,481 Notice of Allowance mailed Sep. 20, 2010", 7 pgs.

"U.S. Appl. No. 11/459,481 Restriction Requirement mailed Jan. 29, 2010", 6 pgs.

"U.S. Appl. No. 11/459,481, Final Office Action mailed May 17, 2010", 11 pgs.

"U.S. Appl. No. 11/459,481, Non-Final Office Action mailed May 28, 2009", 10 pgs.

"U.S. Appl. No. 11/459,481, Response filed Jan. 29, 2009 to Restriction Requirement mailed Dec. 30, 2008", 10 pgs.

"U.S. Appl. No. 11/459,481, Response filed Feb. 10, 2010 to Restriction Requirement mailed Jan. 29, 2010", 8 pgs.

"U.S. Appl. No. 11/459,481, Response filed Aug. 17, 2010 to Final Office Action mailed May 17, 2010", 9 pgs.

"U.S. Appl. No. 11/459,481, Response filed Nov. 25, 2009 to Non Final Office Action mailed May 28, 2009", 14 pgs.

"U.S. Appl. No. 11/459,481, Restriction Requirement mailed Dec. 30, 2008", 7 pgs.

"U.S. Appl. No. 11/482,635, Preliminary Statement Oct. 31, 2006", 2 pgs.

"U.S. Appl. No. 11/558,083, Response filed Dec. 22, 2009 to Non-Final Office Action mailed Jun. 26, 2009", 15 pgs.

"U.S. Appl. No. 11/868,408, Preliminary Amendment filed Oct. 5, 2007", 2 pgs.

"U.S. Appl. No. 12/148,843, Non Final Office Action mailed May 31, 2011", 8 pgs.

"U.S. Appl. No. 12/148,843, Notice of Allowance mailed Oct. 27, 2011", 10 pgs.

"U.S. Appl. No. 12/148,843, Response filed Aug. 30, 2011 to Non Final Office Action mailed May 31, 2011", 9 pgs.

"U.S. Appl. No. 12/148,843, Response filed Apr. 14, 2011 to Restriction Requirement mailed Mar. 15, 2011", 10 pgs.

"U.S. Appl. No. 12/148,843, Restriction Requirement mailed Mar. 15, 2011", 9 pgs.

"U.S. Appl. No. 12/688,575, Response to Restriction Requirement mailed Mar. 30, 2012", 14 pgs.

"U.S. Appl. No. 12/688,575, Restriction Requirement mailed Mar. 30, 2012", 26 pgs.

"U.S. Appl. No. 13/397,115, Response filed Feb. 19, 2013 to Non Final Office Action mailed Nov. 21, 2012", 13 pgs.

"U.S. Appl. No. 13/397,115, Non Final Office Action mailed Nov. 21, 2012", 10 pgs.

"U.S. Appl. No. 13/397,115, Notice of Allowance mailed Apr. 3, 2013", 6 pgs.

"European Application Serial No. 06752356.3, Office Action mailed Apr. 1, 2008", 6 pgs.

(56) References Cited

OTHER PUBLICATIONS

"European Application Serial No. 06752356.3, Response filed Sep. 11, 2008 to Communication mailed Apr. 1, 2008", 17 pgs.

"European Application Serial No. 06827323.4, Communication mailed Jun. 2, 2009", 2 pgs.

"European Application Serial No. 06827323.4, Communication mailed Nov. 12, 2008.", 3 pgs.

"European Application Serial No. 06827323.4, Response filed Apr. 24, 2009 to Communication mailed Nov. 12, 2008", 6 pgs.

"European Application Serial No. 06827323.4, Summons to Attend Oral Proceedings mailed May 19, 2010", 3 pgs.

"European Application Serial No. 06827323.4, Written Submissions filed Sep. 23, 2010", 4 pgs.

"International Application Serial No. PCT/US2006/042727, International Search Report and Written Opinion mailed Apr. 23, 2007", 16 pgs.

"International Application Serial No. PCT/US2006/011446, International Search Report and Written Opinion mailed Aug. 25, 2006", (2006), 14 pgs.

"International Application Serial No. PCT/US2006/017539, International Search Report and Written Opinion mailed Sep. 1, 2006", 12 pgs.

"International Application Serial No. PCT/US2006/017637, International Search Report and Written Opinion mailed Oct. 20, 2006".

"International Application Serial No. PCT/US2010/059252, International Search Report mailed Mar. 2, 2011", 4 pgs.

"International Application Serial No. PCT/US2010/059252, Written Opinion mailed Mar. 2, 2011", 7 pgs.

"International Application Serial No. PCT/US2011/021154, Search Report mailed Mar. 10, 2011", 5 pgs.

"International Application Serial No. PCT/US2011/021154, Written Opinion mailed Mar. 10, 2011", 9 pgs.

"International Search Report and Written Opinion for Application No. PCT/US2006/008314, dated Jul. 6, 2006", 13 pgs.

"Japanese Application Serial No. 2008-511206, Office Action mailed May 17, 2012", With English Translation, 7 pgs.

"Japanese Application Serial No. 2008-511206, Office Action mailed Nov. 11, 2011", With English Translation, With English Translation, 7 pgs.

"Japanese Application Serial No. 2008-511206, Office Action Response filed Mar. 9, 2012", With English Translation, 12 pgs.

"Japanese Application Serial No. 2008-547225, Office Action mailed Nov. 29, 2011", W/ English Translation, 4 pgs.

"Japanese Application Serial No. 2008-547225, Response filed Feb. 29, 2012 to Office Action mailed Nov. 29, 2011", (w/ English Translation of Claims), 16 pgs.

Andersen, H, et al., "Long-term follow-up of patients from a randomised trial of atrial versus ventricular pacing for sick-sinus syndrome", Lancet, 350(9086), (Oct. 25, 1997), 1210-6.

Benchimol, A, et al., "Cardiac hemodynamics during stimulation of the right atrium, right ventricle, and left ventricle in normal and abnormal hearts", Circulation, 33(6), (Jun. 1966), 933-44.

Bevan, J A, et al., "Postganglionic sympathetic delay in vascular smooth muscle", Journal of Pharmacology & Experimental Therapeutics, 152(2), (May 1966), 221-30.

Bevan, J A, et al., "Sympathetic nerve-free vascular muscle", Journal of Pharmacology & Experimental Therapeutics, 157(1), (Jul. 1967), 117-24.

Bilgutay, A M, et al., "A new concept in the treatment of hypertension utilizing an implantable electronic device: "Baropacer"", Trans Am Soc Artif Intern Organs., 10, (1964), 387-395.

Bilgutay, A M, et al., "Vagal tuning for the control of supraventricular arrhythmias", Surgical Forum, 16, (1965), 151-3.

Bilgutay, A. M, et al., "Vagal tuning. A new concept in the treatment of supraventricular arrhythmias, angina pectoris, and heart failure", Journal of Thoracic and Cardiovascular Surgery, 56(1), (Jul. 1968), 71-82.

Borst, C, et al., "Optimal frequency of carotid sinus nerve stimulation in treatment of angina pectoris", Cardiovascular Research, 8(5), (Sep. 1974), 674-80.

Braunwald, E, et al., "Carotid sinus nerve stimulation in the treatment of angina pectoris and supraventricular tachycardia", California Medicine, 112(3), (Mar. 1970), 41-50.

Braunwald, E, et al., "Relief of angina pectoris by electrical stimulation of the carotid-sinus nerves", New England Journal of Medicine, 277(24), (Dec. 14, 1967), 1278-83.

Caparso, Anthony, et al., "System for Neural Control of Respiration", U.S. Appl. No. 11/151,122, filed Jun. 13, 2005, 28 pgs.

Caparso, Anthony, "System for Selective Activation of a Nerve Trunk Using a Transvascular Reshaping Lead", U.S. Appl. No. 11/130,022, filed May 16, 2005, 33 pgs.

Caparso, Anthony, et al., "Vascularly Stabilized Peripheral Nerve Cup Assembly", U.S. Appl. No. 11/151,103, filed Jun. 13, 2005, 41 pgs.

Chapleau, M W, et al., "Pulsatile activation of baroreceptors causes central facilitation of baroreflex", American Journal of Physiology, 256(6 Pt 2), (Jun. 1989), H1735-41.

Chapleau, M. W., et al., "Contrasting effects of static and pulsatile pressure on carotid baroreceptor activity in dogs", Circulation, vol. 61, No. 5, (Nov. 1987), 648-658.

Coleridge, J C, et al., "Relationship between pulmonary arterial pressure and impulse activity in pulmonary arterial baroreceptor fibres", Journal of Physiology, 158, (Sep. 1961), 197-205.

Coleridge, J C, et al., "The distribution, connexions and histology of baroreceptors in the pulmonary artery, with some observations on the sensory innervation of the ductus arteriosus", Journal of Physiology, 156, (May 1961), 591-602.

Cooper, Terry B, et al., "Neural effects on sinus rate and atrioventricular conduction produced by electrical stimulation from a transvenous electrode catheter in the canine right pulmonary artery", Circulation Research, vol. 46, No. 1, (Jan. 1980), 48-57.

Courtice, G P, et al., "Effect of frequency and impulse pattern on the non-cholinergic cardiac response to vagal stimulation in the toad, Bufo marinus", Journal of the Autonomic Nervous System, 48(3), (Aug. 1994), 267-72.

Cyberonics, "NeuroCybernetic Prosthesis System NCPA Pulse Generator Models 100 and 101", Physician's Manual, (Aug. 2002), 1-146.

Dart, Jr., C H, et al., "Carotid sinus nerve stimulation treatment of angina refractory to other surgical procedures", Annals of Thoracic Surgery, 11(4), (Apr. 1971), 348-59.

De Landsheere, D, et al., "Effect of spinal cord stimulation on regional myocardial perfusion assessed by positron emission tomography", American Journal of Cardiology, 69(14), (May 1, 1992), 1143-9.

Dunning, A. J., "Electrostimulation of the Carotid Sinus Nerve in Angina Pectoris", University Department of Medicine, Binnengasthuis, Amsterdam; Printed by Royal VanGorcum, Assen, Netherlands, (1971), 1-92.

Epstein, S. E., et al., "Treatment of angina pectoris by electrical stimulation of the carotid-sinus nerves", New England Journal of Medicine, 280(18), (May 1, 1969), 971-978.

Farrehi, C, "Stimulation of the carotid sinus nerve in treatment of angina pectoris", American Heart Journal, 80(6), (Dec. 1970), 759-65.

Feliciano, L, et al., "Vagal nerve stimulation releases vasoactive intestinal peptide which significantly increases coronary artery blood flow", Cardiovascular Research, 40(1), (Oct. 1998), 45-55.

Fromer, M, et al., "Ultrarapid subthreshold stimulation for termination of atrioventricular node reentrant tachycardia", Journal of the American College of Cardiology, 20(4), (Oct. 1992), 879-83.

Grassi, Guido, et al., "Baroreflex and non-baroreflex modulation of vagal cardiac control after myocardial infarction", Am J Cardiol., 84(5), (Sep. 1, 1999), 525-529.

Griffith, Lawrence S.C., et al., "Electrical Stimulation of the Carotid Sinus Nerve in Normotensive and Renal Hypertensive Dogs", Circulation, 28, (Jul.-Dec. 1963), 730.

Henning, R J, et al., "Effects of autonomic nerve stimulation, asynchrony, and load on dP/dtmax and on dP/dtmin", American Journal of Physiology, 260(4 Pt 2), (Apr. 1991), H1290-H1298.

Henning, R J, et al., "Vagal nerve stimulation increases right ventricular contraction and relaxation and heart rate", Cardiovascular Research, 32(5), (Nov. 1996), 846-53.

(56) References Cited

OTHER PUBLICATIONS

Henning, R J, et al., "Vagal stimulation attenuates sympathetic enhancement of left ventricular function", American Journal of Physiology, 258(5 Pt 2), (May 1990), H1470-5.

Holder, L K, "Treatment of refractory partial seizures: preliminary results of a controlled study", Pacing & Clinical Electrophysiology, 15(10 Pt 2), (Oct. 1992), 1557-71.

Holmgren, C., et al., "Risk of interference from transcutaneous electrical nerve stimulation on the sensing function of implantable defibrillators", Pacing Clin Electrophysiol., 31(2), (Feb. 2008), 151-8.

Hood Jr., W B, et al., "Asynchronous contraction due to late systolic bulging at left ventricular pacing sites", American Journal of Physiology, 217(1), (Jul. 1969), 215-21.

Ishise, H, et al., "Time course of sympathovagal imbalance and left ventricular dysfunction in conscious dogs with heart failure", Journal of Applied Physiology, 84(4), (Apr. 1998), 1234-41.

Janes, R. D., et al., "Anatomy of human extrinsic cardiac nerves and ganglia.", Am J Cardiol., 57(4), (Feb. 1, 1986), 299-309.

Jessurun, G A, et al., "Coronary blood flow dynamics during transcutaneous electrical nerve stimulation for stable angina pectoris associated with severe narrowing of one major coronary artery", American Journal of Cardiology, 82(8), erratum appears in Am J Cardiol Feb. 15, 1999;83(4):642, (Oct. 15, 1998), 921-6.

Kandel, Eric R, et al., "Part VII: Arousal, Emotion, and Behavioral Homeostasis", In: Principles of Neural Science, New York : McGraw-Hill, Health Professions Division, (2000), 966-969.

Karpawich, P P, et al., "Altered cardiac histology following apical right ventricular pacing in patients with congenital atrioventricular block", Pacing Clin Electrophysiol., 22(9), (Sep. 1999), 1372-7.

Kendrick, J E, "A comparison of the cardiovascular responses to stimulation of the aortic and carotid sinus nerves of the dog", Proceedings of the Society for Experimental Biology & Medicine, 144(2), (Nov. 1973), 404-11.

Lacanette, Kerry, "A Basic Introduction to Filters—Active, Passive, and Switched-Capacitor", National Semiconductor Corporation, http://www.swarthmore.edu/NatSci/echeeve1/Ref/DataSheet/Inttofilters.pdf, (Apr. 1991), 1-22.

Leclercq, C, et al., "Hemodynamic importance of preserving the normal sequence of ventricular activation in permanent cardiac pacing", Am Heart J., 129(6), (Jun. 1995), 1133-41.

Leutmezer, F, et al., "Electrocardiographic Changes at the onset of Epileptic Seizures", Epilepsia, 44(3), (2003), 348-354.

Levy, M. N., et al., "Effects of Repetitive Bursts of Vagal Activity on Heart Rate", Circulation Research, 30(2), (1972), 186-195.

Li, M., et al., "Vagal nerve stimulation markedly improves long-term survival after chronic heart failure in rats", Circulation, 109(1), (2004), 120-124.

Libbus, I., "Integrated Lead for Applying Cardiac Resynchronization Therapy and Neural Stimulation Therapy", U.S. Appl. No. 11/077,970, filed Mar. 11, 2005, 67 pgs.

Libbus, I., et al., "Method and Apparatus for Synchronizing Neural Simulation to Cardiac Cycles", U.S. Appl. No. 11/099,141, filed Apr. 5, 2005, 36 pgs.

Libbus, I., "Safety Control System for Implantable Neural Stimulator", U.S. Appl. No. 11/135,883, filed May 24, 2005, 43 pgs.

Libbus, I., et al., "System and Method for Closed-Loop Neural Stimulation", U.S. Appl. No. 10/992,319, filed Nov. 18, 2004, 50 pgs.

Libbus, Imad, "Cardiac Rhythm Management Device With Neural Sensor", U.S. Appl. No. 10/992,320, filed Nov. 18, 2004, 65 pgs.

Libbus, Imad, et al., "Cell Therapy and Neural Stimulation for Cardiac Repair", U.S. Appl. No. 11/063,170, filed Feb. 22, 2005, 42 pgs.

Libbus, Imad, "Implantable Device for Treating Epilepsy and Cardiac Rhythm Disorders", U.S. Appl. No. 11/312,178, filed Dec. 21, 2005, 39 pgs.

Libbus, Imad, et al., "Implantable Neural Stimulator With Mode Switching", U.S. Appl. No. 11/137,038, filed May 25, 2005, 42 pgs.

Libbus, Imad, et al., "Method and Apparatus for Controlling Autonomic Balance Using Neural Stimulation", U.S. Appl. No. 11/124,791, filed May 9, 2005, 47 pgs.

Libbus, Imad, "Method and Apparatus for Simultaneously Presenting Cardiac and Neural Signals", U.S. Appl. No. 11/114,246, filed Apr. 25, 2005, 58 pgs.

Libbus, Imad, et al., "Neural Stimulation System to Prevent Simultaneous Energy Discharges", U.S. Appl. No. 11/110,542, filed Apr. 20, 2005, 36 pgs.

Libbus, Imad, "Neural Stimulation With Avoidance of Inappropriate Stimulation", U.S. Appl. No. 11/000,249, filed Nov. 30, 2004, 45 pgs.

Libbus, Imad, "Stimulator for Auricular Branch of Vagus Nerve", U.S. Appl. No. 11/005,703, filed Dec. 7, 2004, 35 pgs.

Libbus, Imad, et al., "System and Method for Filtering Neural Stimulation", U.S. Appl. No. 10/982,001, filed Nov. 4, 2004, 58 pgs.

Libbus, Imad, "System and Method to Deliver Therapy in Presence of Another Therapy", U.S. Appl. No. 11/125,503, filed May 10, 2005, 39 pgs.

Libbus, Imad, "System to Provide Myocardial and Neural Stimulation", U.S. Appl. No. 11/087,935, filed Mar. 23, 2005, 52 pgs.

Libbus, Imad, "System to Provide Neural Markers for Sensed Neural Activity", U.S. Appl. No. 11/113,773, filed Apr. 25, 2005, 52 pgs.

Mannheimer, C, et al., "Epidural spinal electrical stimulation in severe angina pectoris", British Heart Journal, 59(1), (Jan. 1988), 56-61.

Mannheimer, C, et al., "Transcutaneous electrical nerve stimulation (TENS) in angina pectoris", Pain, 26(3), (Sep. 1986), 291-300.

Mannheimer, C, et al., "Transcutaneous electrical nerve stimulation in severe angina pectoris", European Heart Journal, 3(4), (Aug. 1982), 297-302.

Martin, P., "Time-dependent heart period and contractility responses to successive brief vagal stimuli", Am J Physiol, 239(4), (Oct. 1980), H494-H500.

Mazgalev, T N, et al., "Autonomic modification of the atrioventricular node during atrial fibrillation: role in the slowing of ventricular rate", Circulation, 99(21), (Jun. 1, 1999), 2806-14.

McGregor, A., et al., "Right-Sided Vagus Nerve Stimulation as a Treatment for Refractory Epilepsy in Humans", Epilepsia; 46(1), (Jan. 2005), 91-96.

Millar-Craig, M W, et al., "Circadian variation of blood-pressure", Lancet, 1(8068), (Apr. 15, 1978), 795-7.

Minisi, A J, et al., "Regional left ventricular deafferentation increases baroreflex sensitivity following myocardial infarction", Cardiovasc Res., 58(1), (Apr. 1, 2003), 136-41.

Moffitt, Julia, "Combined Neural Stimulation and Cardiac Resynchronization Therapy", U.S. Appl. No. 11/078,460, filed Mar. 11, 2005, 35 pgs.

Moffitt, Julia, et al., "Neural Stimulator System for Cardiac Fat Pads", U.S. Appl. No. 11/077,583, filed Mar. 11, 2005, 37 pgs.

Moffitt, Julia, et al., "System to Treat AV-Conducted Ventricular Tachyarrhythmia", U.S. Appl. No. 11/099,226, filed Apr. 5, 2005, 39 pgs.

Moffitt, Julia, "Transvascular Neural Stimulation Device", U.S. Appl. No. 11/103,245, filed Apr. 11, 2005, 33 pgs.

Murphy, D F, et al., "Intractable angina pectoris: management with dorsal column stimulation", Medical Journal of Australia, 146(5), (Mar. 2, 1987), 260.

Neistadt, A, et al., "Effects of electrical stimulation of the carotid sinus nerve in reversal of experimentally induced hypertension", Surgery, 61(6), (Jun. 1967), 923-31.

Nolan, J., et al., "Prospective Study of Heart Rate Variability and Mortality in Chronic Heart Failure: Results of the United Kingdom Heart Failure Evaluation and Assessment of Risk Trial (UK-Heart).", Circulation, 98(15), (1998), 1510-1516.

Peters, T K, et al., "Temporal and spatial summation caused by aortic nerve stimulation in rabbits. Effects of stimulation frequencies and amplitudes", Journal of the Autonomic Nervous System, 27(3), (Aug. 1989), 193-205.

Peters, T K, et al., "The principle of electrical carotid sinus nerve stimulation: a nerve pacemaker system for angina pectoris and hypertension therapy", Annals of Biomedical Engineering, 8(4-6), (1980), 445-458.

Philbin, D M, et al., "Inappropriate shocks delivered by an ICD as a result of sensed potentials from a transcutaneous electronic nerve stimulation unit", Pacing & Clinical Electrophysiology, 21(10), (Oct. 1998), 2010-1.

(56) References Cited

OTHER PUBLICATIONS

Prakash, P, et al., "Asymmetrical distribution of aortic nerve fibers in the pig", Anat Rec., 158(1), (May 1967), 51-7.

Rosenqvist, M, et al., "The effect of ventricular activation sequence on cardiac performance during pacing", Pacing and Electrophysiology, 19(9), (1996), 1279-1286.

Rugg-Gunn, F. J, et al., "Cardiac arrhythmias in focal epilepsy: a prospective long-term study.", Lancet, 364(9452), (Dec. 18-31, 2004), 2212-9.

Rushmer, Robert F, "Chapter 5—Systemic Arterial Pressure", In: Cardiovascular dynamics, Philadelphia : Saunders, (1976), 176-216.

Schauerte, P, et al., "Catheter stimulation of cardiac parasympathetic nerves in humans: a novel approach to the cardiac autonomic nervous system", Circulation, 104(20), (Nov. 13, 2001), 2430-5.

Schauerte, P, et al., "Ventricular rate control during atrial fibrillation by cardiac parasympathetic nerve stimulation: a transvenous approach", J Am Coll Cardiol., 34(7), (Dec. 1999), 2043-50.

Schauerte, P. N, et al., "Transvenous parasympathetic cardiac nerve stimulation: an approach for stable sinus rate control", Journal of Cardiovascular Electrophysiology, 10(11), (Nov. 1999), 1517-1524.

Schauerte, P., et al., "Transvenous parasympathetic nerve stimulation in the inferior vena cava and atrioventricular conduction", Journal of Cardiovascular Electrophysiology, 11(1), (Jan. 2000), 1 pg.

Scheiner, Avram, et al., "Leads for Pacing and/or Sensing the Heart From Within the Coronary Veins", U.S. Appl. No. 11/600,807, filed Nov. 16, 2006, 43 pgs.

Scherlag, B. J, et al., "Endovascular stimulation within the left pulmonary artery to induce slowing of heart rate and paroxysmal atrial fibrillation.", Cardiovasc Research, 54(2), (May 2002), 470-475.

Scherlag, M A., et al., "Endovascular Neural Stimulation Via a Novel Basket Electrode Catheter: Comparison of Electrode Configurations", Journal of Interventional Cardiac Electrophysiology, 4(1), (Apr. 2000), 219-224.

Sigurdsson, A., et al., "The Role of Neurohormonal Activation in Chronic Heart Failure and Postmyocardial Infarction", American Heart Journal, 132(1, Part 2), (Jul. 1996), 229-234.

Takahashi, N, et al., "Vagal modulation of ventricular tachyarrhythmias induced by left ansae subclaviae stimulation in rabbits", Japanese Heart Journal, 39(4), (Jul. 1998), 503-11.

Thompson, Gregory W, "Bradycardia induced by intravascular versus direct stimulation of the vagus nerve", Annals of Thoracic Surgery, 65(3), (Mar. 1998), 637-642.

Tse, H F, et al., "Long-term effect of right ventricular pacing on myocardial perfusion and function", J Am Coll Cardiol., 29(4), (Mar. 15, 1997), 744-9.

Vanoli, E., et al., "Vagal Stimulation and Prevention of Sudden Death in Conscious Dogs With a Healed Myocardial Infarction", Circulation Research, 68(5), (May 1991), 1471-1481.

Veerman, D P, et al., "Circadian profile of systemic hemodynamics", Hypertension, 26(1), (Jul. 1995), 55-9.

Verity, M A, et al., "Plurivesicular nerve endings in the pulmonary artery", Nature, 211(48), (Jul. 30, 1966), 537-8.

Verity, M, et al., "Pulmonary artery innervation: a morphopharmacologic correlation", Proceedings of the Western Pharmacology Society, 8, (1965), 57-9.

Wallick, D W, et al., "Selective AV nodal vagal stimulation improves hemodynamics during acute atrial fibrillation in dogs", American Journal of Physiology—Heart & Circulatory Physiology, 281(4), (Oct. 2001), H1490-7.

Waninger, M S, et al., "Electrophysiological control of ventricular rate during atrial fibrillation", Pacing & Clinical Electrophysiology, 23(8), (Aug. 2000), 1239-44.

Wiggers, C J, et al., "The muscular reactions of the mammalian ventricles to artificial surface stimuli", American Journal of Physiology, (1925), 346-378.

Zhang, Y, et al., "Optimal ventricular rate slowing during atrial fibrillation by feedback AV nodal-selective vagal stimulation", American Journal of Physiology—Heart & Circulatory Physiology, 282(3), (Mar. 2002), H1102-10.

Zhou, X, et al., "Prevention of high incidence of neurally mediated ventricular arrhythmias by afferent nerve stimulation in dogs", Circulation, 101(7), (Feb. 22, 2000), 819-24.

US 8,805,494 B2

SYSTEM AND METHOD TO DELIVER THERAPY IN PRESENCE OF ANOTHER THERAPY

CLAIM OF PRIORITY

This application is a continuation of U.S. application Ser. No. 13/397,115, filed Feb. 15, 2012, now U.S. Pat. No. 8,504,149, which is a divisional of U.S. application Ser. No. 12/148,843,filed Apr. 23, 2008, now U.S. Pat. No. 8,131,359, which is a divisional of U.S. application Ser. No. 11/125,503, filed May 10, 2005, now U.S. Pat. No. 7,493,161, the specifications of which are herein incorporated by reference.

TECHNICAL FIELD

This application relates generally to medical devices and, more particularly, to systems, devices and methods to control the delivery of therapy.

BACKGROUND

Different types of therapies can be delivered simultaneously, or near simultaneously, to treat the same condition or to treat different conditions. For example, it is possible to deliver both neural stimulation (NS) therapy and cardiac rhythm management (CRM) therapy.

Some NS therapy can alter cardiac contractility and excitability. Direct electrical stimulation of parasympathetic nerves can activate the baroreflex, inducing a reduction of sympathetic nerve activity and reducing blood pressure by decreasing vascular resistance. Sympathetic inhibition, as well as parasympathetic activation, have been associated with reduced arrhythmia vulnerability following a myocardial infarction, presumably by increasing collateral perfusion of the acutely ischemic myocardium and decreasing myocardial damage. Modulation of the sympathetic and parasympathetic nervous system with neural stimulation has been shown to have positive clinical benefits, such as protecting the myocardium from further remodeling and predisposition to fatal arrhythmias following a myocardial infarction.

SUMMARY

Various aspects of the present subject matter relate to a device. In various embodiments, the device comprises at least one port to connect to at least one lead with at least one electrode, stimulator circuitry connected to the at least one port and adapted to deliver electrical pulses to at least one of the electrodes as part of a first electrical therapy type, and a controller connected to the stimulator circuitry. The controller is adapted to control delivery of the electrical pulses using a plurality of parameters for at least one programmed electrical therapy of the first electrical therapy type. The controller is adapted to determine when a therapy of a second electrical therapy type is applied, provide electrical therapy for the first electrical therapy type using a first set of parameters when the therapy of the second electrical therapy type is present to affect the at least one programmed electrical therapy for the first electrical therapy type, and provide electrical therapy using a second set of parameters when the therapy of the second electrical therapy type is not present.

Various aspects of the present subject matter relate to a method. In various embodiments, a therapy of a first therapy type is delivered, and it is identified whether a therapy of a second therapy type is present to affect the therapy of the first therapy type. Delivery of the therapy is controlled based on the presence of the therapy of the second therapy type. Some embodiments deliver the therapy of the first type using one set of parameters in the presence of a therapy of a second type, and deliver the therapy of the first type using another set of parameters when the therapy of the second type is not present.

In various embodiments, the first therapy type includes a cardiac rhythm management therapy, and the second therapy type includes a neural stimulation therapy. In various embodiments, the first therapy type includes a neural stimulation therapy and the second therapy type includes a cardiac rhythm management therapy.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1:
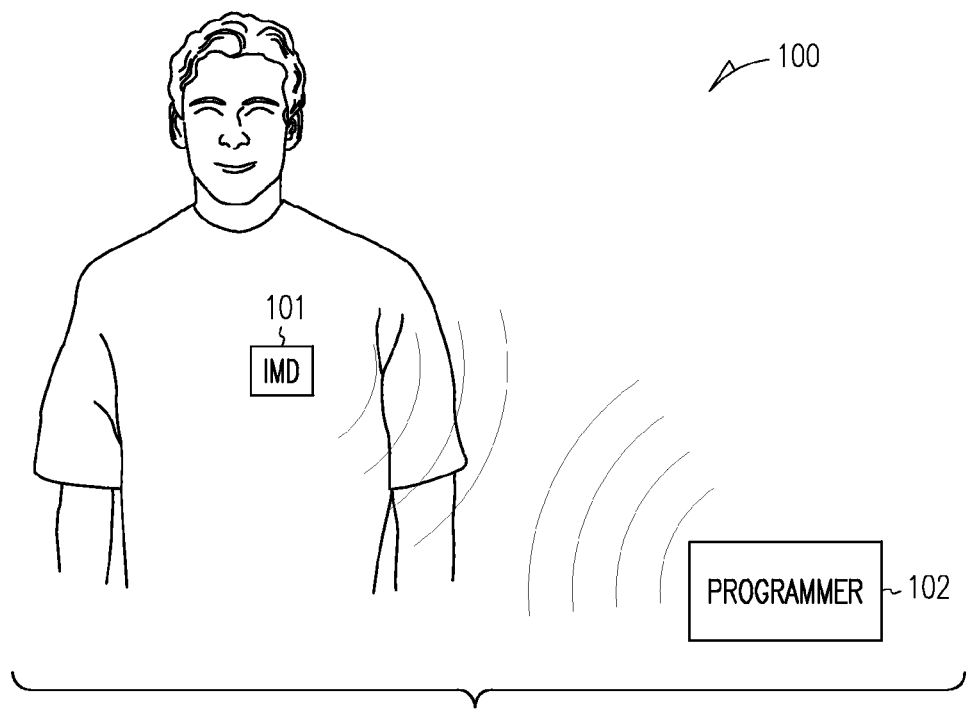
FIG. 1 illustrates a system including an implantable medical device (IMD) and a programmer, according to various embodiments.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The present subject matter relates to a device that delivers a therapy of a first therapy type, identifies whether a therapy of a second therapy type is present to affect the therapy of the first therapy type, and controls delivery of the therapy based on the presence of the therapy of the second therapy type and based on a plurality of parameters organized into a first set and a second set in at least one programmed therapy for the therapy type. Some embodiments of the present subject matter relates to a device that provides a cardiac rhythm management (CRM) type of therapy, such as a pacing therapy and various pacing modes, a defibrillation therapy, and a cardiac resynchronization therapy (CRT), and combinations thereof. The CRM type of therapy is provided in the presence of neural stimulation (NS) therapy. The CRM and NS therapy can be contained in the same device or in independent implantable devices that communicate through lead-based or leadless means.

In various embodiments, the CRM device detects, receives an alert or otherwise identifies the presence of neural stimulation, and switches from a first to a second set of pacing and/or defibrillation parameters to account for the presence of neural stimulation. It is known that some neural stimulation can alter, among other things, cardiac conduction, contractility and excitability. The use of the second set of parameters accounts for such changes induced by the neural stimulation.

In various embodiments, the neural stimulation device detects, receives an alert or otherwise identifies the presence of the CRM device, and switches from a first to a second set of neural stimulation parameters. CRM therapy captures cardiac tissue with electrical energy. The electrical energy itself can cause problems. An example of switching from a first set of parameter to a second set of parameters includes stimulating a different neural target, or changing a neural stimulation signal parameter, such as amplitude, frequency, burst timing and morphology, to compensate for the CRM therapy. Another example provides a neural stimulation therapy to cooperate with CRM therapy, such as by stimulating an SVC-AO cardiac fat pad to selectively control contractility for the heart, a PV cardiac fat pad associated with an sinoatrial (SA) node to selectively control a sinus rate, and/or an IVC-LA cardiac fat pad associated with an atrioventricular (AV) node to selectively control AV conduction. In humans, the SVC-AO cardiac fat pad is located proximate to a junction between a superior vena cava and an aorta, the PV cardiac fat pad is located proximate to a junction between a right atrium and right pulmonary vein, and the IVC-LA cardiac fat pad is located proximate to a junction between an inferior vena cava and left atrium. Because fat pad ganglia form part of the efferent pathway, stimulation of cardiac fat pads directly effects cardiac tissue. For example, stimulating the parasympathetic efferents can selectively affect rate, and conduction. Stimulation of the parasympathetic pathway also has post-ganglionic inhibition of sympathetic outflow. The cardiac fat pads can be stimulated with epicardial leads with electrodes placed in or near the target fat pad, with intravascularly-fed leads to transvascularly stimulate the target fat pad from within the vessel, and intravascularly fed leads to pierce through a vessel wall into the target fat pad. Neural pathways, such as the vagus nerve trunk and vagal cardiac branches, for example, can be stimulated using a nerve cuff, using an intravascularly-fed leads to transvascularly stimulate the neural target from within the vessel, and intravascularly-fed leads to pierce through a vessel wall into position proximate to a neural target. Baroreceptors within blood vessel walls can be stimulated using an intravascularly-fed lead and a stent-like electrode positioned proximate to the target baroreceptors.

According to various embodiments, the CRM device identifies the presence of neural stimulation (e.g. detects the neural stimulation or is alerted by the neural stimulation device). When neural stimulation is identified the device switches from its normal mode to a "neural stimulation mode." In this mode, the device uses alternate settings for parameters such as V-V interval, A-V interval, anti-tachycardia pacing (ATP) rate, defibrillation threshold, etc. to adapt to the presence of neural stimulation. The second set of parameters are independently programmable in some embodiments. Some embodiments automatically relate the second set of parameters to the baseline parameters.

Since neural stimulation can alter cardiac conduction and excitability. Therefore, the appropriate CRM settings during neural stimulation may be different from the appropriate settings in the absence of neural stimulation. The present subject matter allows the CRM and neural stimulation devices to continuously provide appropriate therapy.

Various embodiments provide a system, either in one device or in more than one device, with capabilities to provide CRM and NS therapy, and with the capability to automatically adjust pacing and defibrillation parameters during neural stimulation to account for altered cardiac conditions. During neural stimulation, some embodiments switch to an alternate set of CRM parameters, compensating for cardiac changes caused by neural stimulation. Therefore, the system has two sets of pacing and defibrillation parameters. The parameters in the sets can be mutually or partially exclusive of each other. The parameters of one set can be a subset of the parameters in another. The sets can include the same parameters, but different values for one or more of the parameters. The second set could be independently programmable or automatically related to the baseline parameters.

FIG. 1 illustrates a system 100 including an implantable medical device (IMD) 101 and a programmer 102, according to various embodiments of the present subject matter. Various embodiments of the IMD 101 include neural stimulator functions only, various embodiments include CRM functions only, and various embodiments include a combination of NS and CRM functions. The IMD can be designed to deliver other therapies, such as drug therapies. The IMD and programmer are capable of wirelessly communicating data and instructions. In various embodiments, for example, the programmer and IMD use telemetry coils to wirelessly communicate data and instructions. Thus, the programmer can be used to adjust the programmed therapy provided by the IMD, and the IMD can report device data (such as battery and lead resistance) and therapy data (such as sense and stimulation data) to the programmer using radio telemetry, for example.

FIG. 1 illustrates an implantable medical device (IMD). Aspects of the present subject matter can be practiced using external devices. FIG. 1 also illustrates that IMD communicating with a programmer. The IMD can also wirelessly communicate directly with a personal digital assistant or other electronic device such as would be used in an advanced patient management (APM) system, which can organize and perform calculations based on recorded data, and later provide the data to a programmer.

Figure 2:
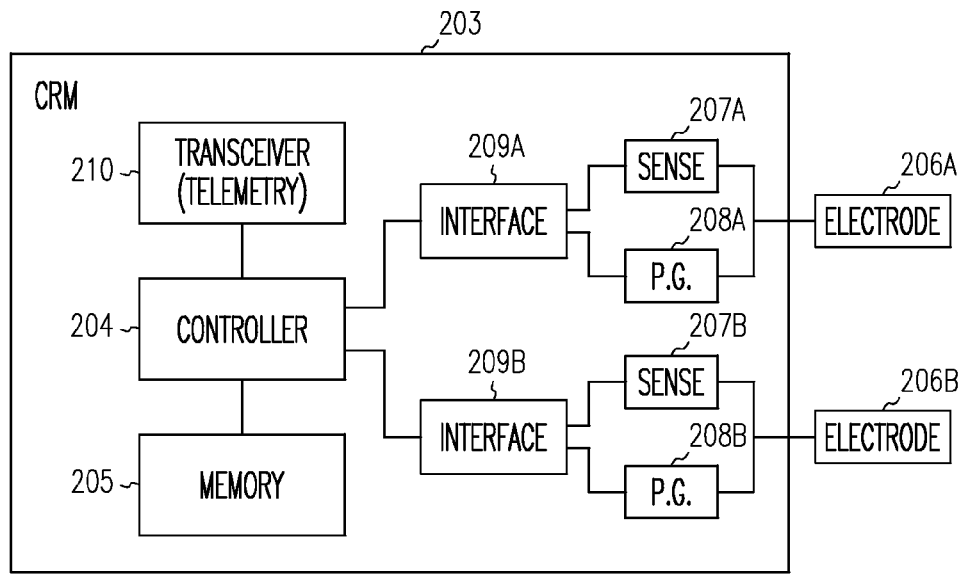
FIG. 2 illustrates an embodiment of CRM device, such as can be used in an IMD in the system of FIG. 1.

FIG. 2 illustrates an embodiment of CRM device 203, such as can be used in an IMD in the system of FIG. 1. The illustrated device 203 includes a controller 204 connected to a memory 205. The figure further illustrates electrodes 206A and 206B connected to the device. According to the illustration, the electrodes 206A and 206B are connected to sense modules 207A and 207B to sense electrical signal at the electrode, and pulse generators 208A and 208B to generate stimulation signals to the electrodes. The controller 204 is connected to the sense modules 207A and 207B and the pulse generator modules 208A and 208B via interfaces 209A and 209B.

The memory includes data and instructions. The controller is adapted to access and operate the instructions to perform various functions within the device, including programmed CRM therapies. The memory 205 includes a plurality of parameters that are used to control the delivery of the therapy. The plurality of parameters are organized into at least two sets. A programmed therapy can be performed using either of the at least two sets of parameters. In various embodiments, the controller operates on the instructions to deliver a therapy, such as bradycardia pacing or defibrillation, of a CRM therapy type is delivered. The controller identifies whether a therapy of a second therapy type, such as a neural stimulation therapy, is present to affect the CRM therapy. Delivery of the CRM therapy is controlled based on the presence of the neural stimulation therapy type. Some embodiments deliver the CRM therapy using one set of parameters in the presence of a neural stimulation therapy and deliver the CRM therapy using another set of parameters when the neural stimulation therapy is not present.

A transceiver 210 is connected to the controller 204. The CRM device is capable of wireless communicating with a programmer, for example, using the transceiver 210. For example, various embodiments use telemetry coils to wirelessly communicate data and instructions. In other embodiments, communication of data and/or energy is by ultrasonic means.

Figure 3:
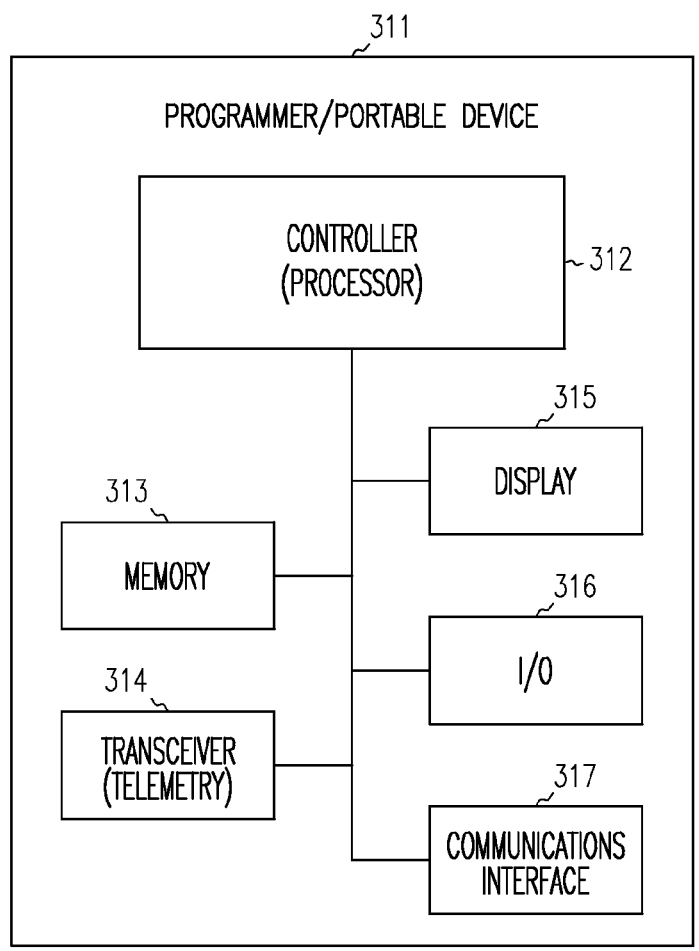
FIG. 3 illustrates a programmer, such as the programmer illustrated in the system of FIG. 1, or other external device to communicate with the implantable medical device(s), according to various embodiments.

FIG. 3 illustrates a programmer 311, such as the programmer 102 illustrated in the system of FIG. 1, or other external device to communicate with the implantable medical device (s), according to various embodiments of the present subject matter. An example of another external device includes Personal Digital Assistants (PDAs) or personal laptop and desktop computers in an Advanced Patient Management (APM) system. The illustrated device includes controller circuitry 312 and a memory 313. The controller circuitry is capable of being implemented using hardware, software, and combinations of hardware and software. For example, according to various embodiments, the controller circuitry includes a processor to perform instructions embedded in the memory to perform a number of functions, including communicating data and/or programming instructions to the implantable devices. The illustrated device 311 further includes a transceiver 314 and associated circuitry for use to communicate with an implantable device. Various embodiments have wireless communication capabilities. For example, various embodiments of the transceiver and associated circuitry include a telemetry coil for use to wirelessly communicate with an implantable device. The illustrated device 311 further includes a display 315, input/output (I/O) devices 316 such as a keyboard or mouse/pointer, and a communications interface 317 for use to communicate with other devices, such as over a communication network.

The programmer is able to program at least some of the parameters in one of the parameter sets used by the IMD to provide the therapy. In some embodiments, the IMD automatically determines the second set of parameters as a function of the programmed first set of parameters. In various embodiments, at least some of the parameters in both a first and second set of parameters is programmable.

Figure 4:
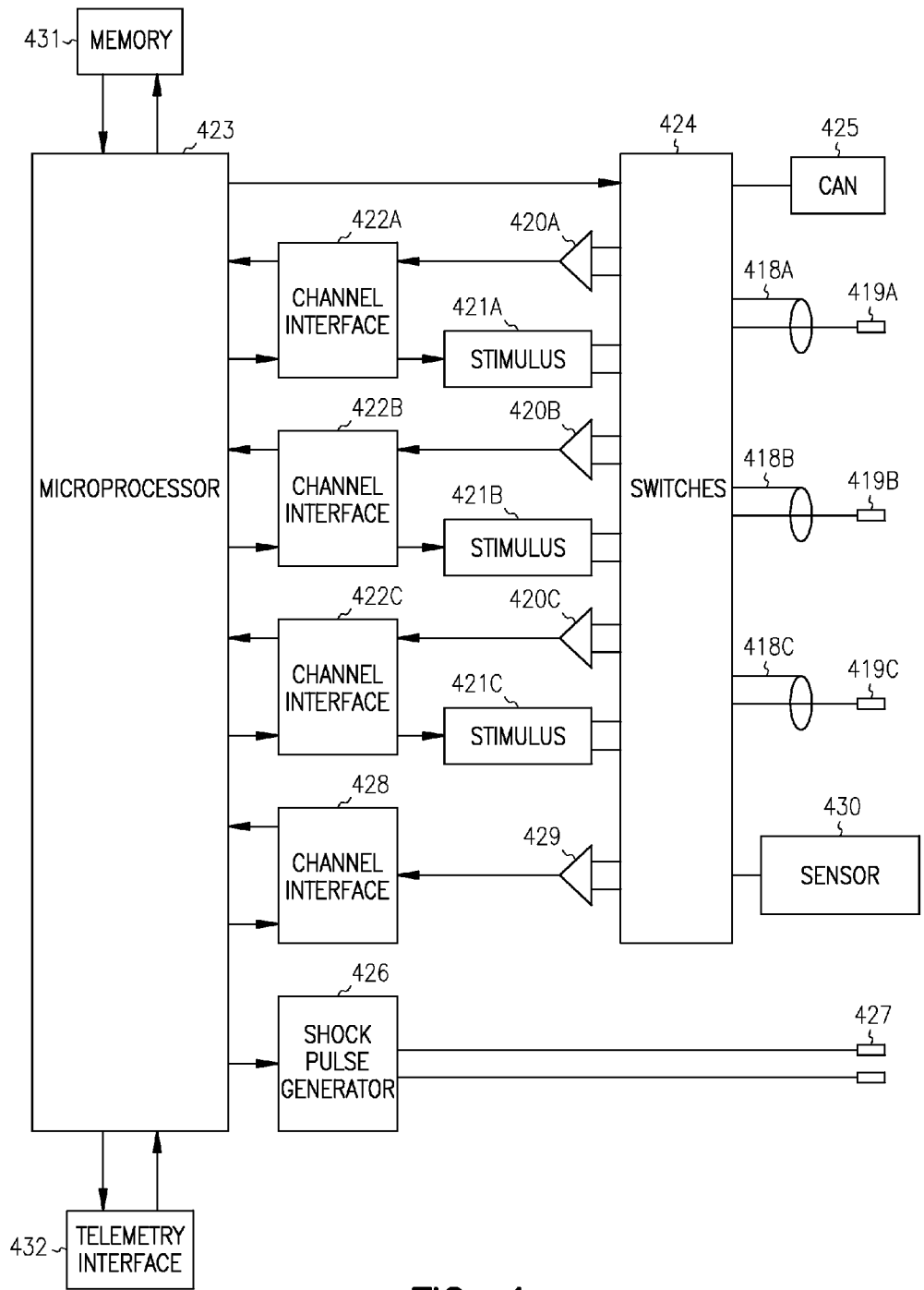
FIG. 4 illustrates a system diagram of an embodiment of an implantable medical device configured for multi-site stimulation and sensing.

FIG. 4 illustrates a system diagram of an embodiment of an implantable medical device configured for multi-site stimulation and sensing. This diagram provides another example of an IMD capable of performing a number of CRM type of therapies. Pacing, as used in the discussion of this figure, relates to electrical stimulation. In various embodiments, the stimulation for a given channel includes stimulation to capture myocardia, neural stimulation or both pacing and neural stimulation. Three examples of sensing and pacing channels are designated "A" through "C". The illustrated channels comprise bipolar leads with ring electrodes 418A-C and tip electrodes 419A-C, sensing amplifiers 420A-C, pulse generators 421A-C, and channel interfaces 422A-C. Each of these channels thus includes a stimulation channel extending between the pulse generator, the electrode and a sensing channel extending between the sense amplifier and the electrode. The channel interfaces 422A-C communicate bidirectionally with microprocessor 423, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry detects a chamber sense, either an atrial sense or ventricular sense, when an electrogram signal (i.e., a voltage sensed by an electrode representing cardiac electrical activity) generated by a particular channel exceeds a specified detection threshold. Algorithms, including a number of adjustable parameters, used in particular stimulation modes employ such senses to trigger or inhibit stimulation, and the intrinsic atrial and/or ventricular rates can be detected by measuring the time intervals between atrial and ventricular senses, respectively. The AV conduction can be measured by measuring a time interval between atrial and ventricular intrinsic events.

The switching network 424 is used to switch the electrodes to the input of a sense amplifier in order to detect intrinsic cardiac activity and to the output of a pulse generator in order to deliver stimulation. The switching network also enables the device to sense or stimulate either in a bipolar mode using both the ring and tip electrodes of a lead or in a unipolar mode using only one of the electrodes of the lead with the device housing or can 425 serving as a ground electrode or another electrode on another lead serving as the ground electrode. A shock pulse generator 426 is also interfaced to the controller for delivering a defibrillation shock via a pair of shock electrodes 427 to the atria or ventricles upon detection of a shockable tachyarrhythmia. Channel interface 428 and sense amplifier 429 provide a connection between the microprocessor and the switch to receive a sensed signal from a sensor 430 for use to detect a second therapy type such as a neural stimulation therapy.

The controller or microprocessor controls the overall operation of the device in accordance with programmed instructions and a number of adjustable parameters stored in memory 431, including controlling the delivery of stimulation via the channels, interpreting sense signals received from the sensing channels, and implementing timers for defining escape intervals and sensory refractory periods. The controller is capable of operating the device in a number of programmed stimulation modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse Inhibited stimulation modes utilize escape intervals to control pacing in accordance with sensed intrinsic activity such that a stimulation pulse is delivered to a heart chamber during a cardiac cycle only after expiration of a defined escape interval during which no intrinsic beat by the chamber is detected. Escape intervals for ventricular stimulation can be restarted by ventricular or atrial events, the latter allowing the pacing to track intrinsic atrial beats. A telemetry interface 432 is also provided which enables the controller to communicate with an external programmer or remote monitor. Rather than or in addition to interface 428, sense amplifier 429 and sensor 430, some embodiments receive an alert or other communication through the telemetry interface or through other communication means to identify the presence of another type of therapy.

Figure 5:
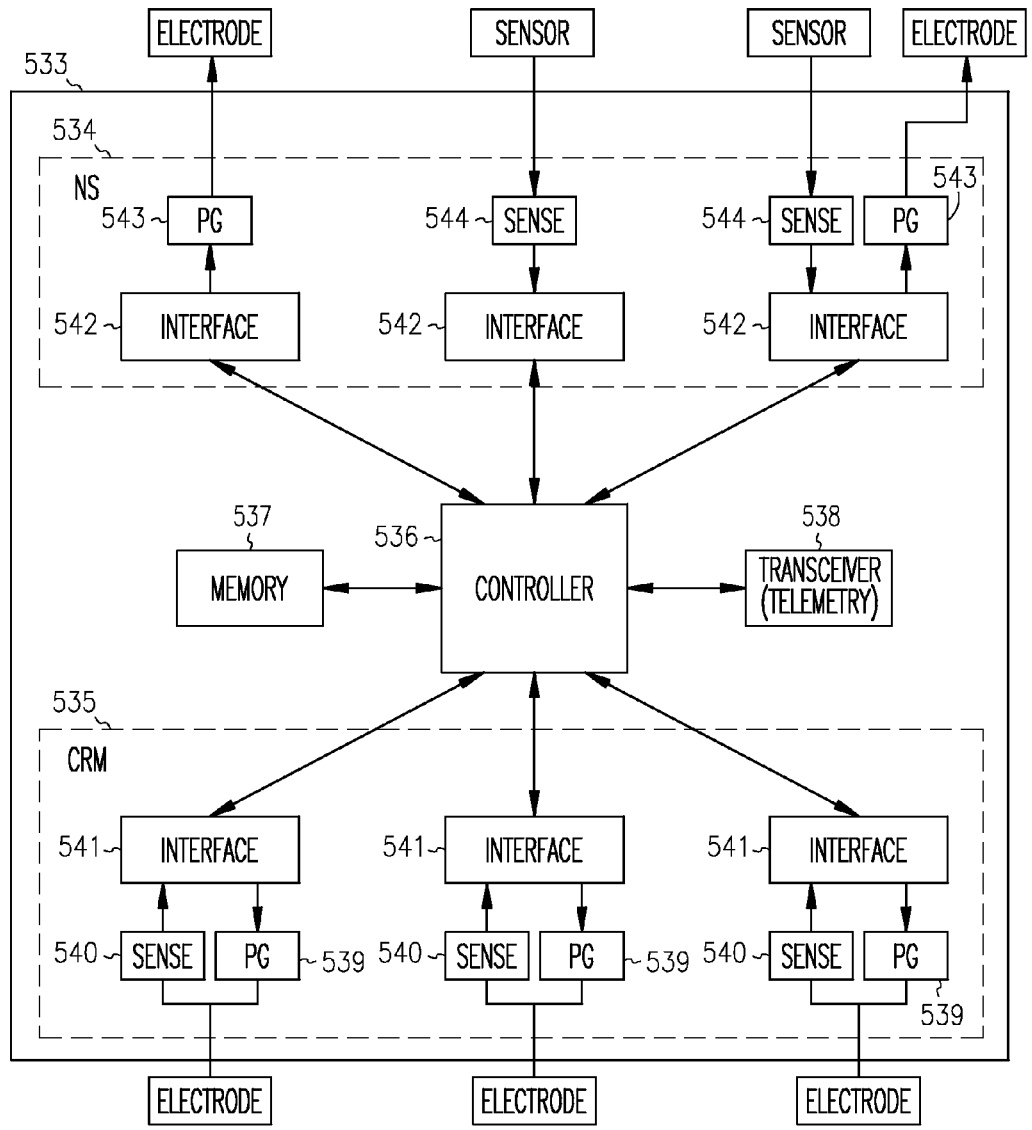
FIG. 5 illustrates an implantable medical device (IMD) such as shown in FIG. 1 having a neural stimulation (NS) component and cardiac rhythm management (CRM) component, according to various embodiments.

FIG. 5 illustrates an implantable medical device (IMD) 533 such as shown at 101 in FIG. 1 having a neural stimulation (NS) component 534 and cardiac rhythm management (CRM) component 535, according to various embodiments of the present subject matter. The illustrated device 533 includes a controller 536 and a memory 537. According to various embodiments, the controller includes hardware, software, or a combination of hardware and software to perform the baroreceptor stimulation and CRM functions. For example, the programmed therapy applications, including a plurality of parameters organized in at least two parameter sets, discussed in this disclosure are capable of being stored as computer-readable instructions embodied in memory and executed by a processor. According to various embodiments, the controller includes a processor to execute instructions embedded in memory to perform the baroreceptor stimulation and CRM functions. The illustrated device 533 further includes a transceiver 538 and associated circuitry for use to communicate with a programmer or another external or internal device. Various embodiments include a telemetry coil.

The CRM therapy section 535 includes components, under the control of the controller, to stimulate a heart and/or sense cardiac signals using one or more electrodes. The CRM therapy section includes a pulse generator 539 for use to provide an electrical signal through an electrode to stimulate a heart, and further includes sense circuitry 540 to detect and process sensed cardiac signals. An interface 541 is generally illustrated for use to communicate between the controller 536 and the pulse generator 539 and sense circuitry 540. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 534 includes components, under the control of the controller, to stimulate a baroreceptor and/or sense ANS parameters associated with nerve activity or surrogates of ANS parameters such as blood pressure and respiration. Three interfaces 542 are illustrated for use to provide ANS therapy. However, the present subject matter is not limited to a particular number interfaces, or to any particular stimulating or sensing functions. Pulse generators 543 are used to provide electrical pulses to an electrode for use to stimulate a baroreceptor site. According to various embodiments, the pulse generator includes circuitry to set, and in some embodiments change, the amplitude of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals. Sense circuits 544 are used to detect and process signals from a sensor, such as a sensor of nerve activity, blood pressure, respiration, and the like. The interfaces 542 are generally illustrated for use to communicate between the controller 536 and the pulse generator 543 and sense circuitry 544. Each interface, for example, may be used to control a separate lead. Various embodiments of the NS therapy section only include a pulse generator to stimulate baroreceptors.

According to various embodiments, the lead(s) and the electrode(s) on the leads are physically arranged with respect to the heart in a fashion that enables the electrodes to properly transmit pulses and sense signals from the heart, and with respect to neural targets to stimulate, and in some embodiments sense neural traffic from, the neural targets. Examples of neural targets include both efferent and afferent pathways, such as baroreceptors, nerve trunks and branches such as the vagus nerve, and cardiac fat pads, to provide a desired neural stimulation therapy. As there may be a number of leads and a number of electrodes per lead, the configuration can be programmed to use a particular electrode or electrodes.

The leads of the device include one or more leads to provide CRM therapy, such as atrial pacing, right and/or left ventricular pacing, and/or defibrillation. The device also contains at least on neural stimulation lead which is placed in an appropriate location. Some embodiments perform neural stimulation and CRM therapy using the same lead. Examples of neural stimulation leads include: an expandable stimulation lead placed in the pulmonary artery in proximity of a high concentration of baroreceptors; an intravascularly-fed lead placed proximate to a cardiac fat pad to transvascularly stimulate the fat pad; an epicardial lead with an electrode placed in or proximate to the fat pad; a cuff electrode placed around the aortic, carotid, or vagus nerve; and an intravascularly-fed lead placed to transvascularly stimulate the aortic, carotid or vagus nerve. Other lead placements to stimulate other neural targets may be used.

The controller controls delivery of the electrical pulses using a plurality of parameters for at least one programmed electrical therapy of a first electrical therapy type. The controller is adapted to determine when a therapy of a second electrical therapy type is applied, which can be sensed or other communicated via an alert signal. The controller provides electrical therapy for the first electrical therapy type using a first set of parameters when the therapy of the second electrical therapy type is present to affect the at least one programmed electrical therapy for the first electrical therapy type, and provides electrical therapy using a second set of parameters when the therapy of the second electrical therapy type is not present.

In some embodiments, the first electrical therapy type is a CRM type of therapy, and the second electrical therapy is a neural stimulation type of therapy. There are a number of therapies of a CRM type. Examples include ventricular defibrillation, atrial defibrillation, pacing such as bradycardia and tachycardia pacing, and cardiac rhythm management therapy. In some embodiments, the second electrical therapy type is a neural stimulation (NS) type of therapy. There are a number of therapies of an NS type. Examples include anti-hypertension therapy, therapy for a myocardial infarction, and stimulation to selectively control cardiac conduction and contractility. In other embodiments, the first electrical therapy type is an NS type and the second electrical therapy type is a CRM type.

A plurality of parameters are used by algorithms performed by the controller to deliver the desired therapy. Often, these parameters are adjustable. A programmer, for example, is able to adjust parameters in an IMD. The present subject matter organizes the parameters into at least two sets for a given therapy of the first type. The parameter set used depends on whether the second therapy type is present. The different parameter sets can represent a different value for at least one of the parameters, or can represent at least one different parameter. The different parameter sets can represent different pacing modes, such as atrial pacing (AOO, AAI), ventricular pacing (VVI, VOO), and or dual chamber pacing (DDI, DDD, VDD), for example. Thus, changing the parameter set can change the pacing mode. Additionally, changing the parameter set can change values for parameters for a particular pacing mode, such as base rate, upper rate, AV interval, ventricular refractory and ventricular blanking in a DDD pacing mode.

In some embodiments, the first electrical therapy type is a NS type of therapy, and the second electrical therapy is a CRM type of therapy. Examples of parameters for neural stimulation include parameters that control location of the neural target, and that control amplitude, frequency, burst timing (such as burst frequency and burst duration), and morphology.

Figure 6:
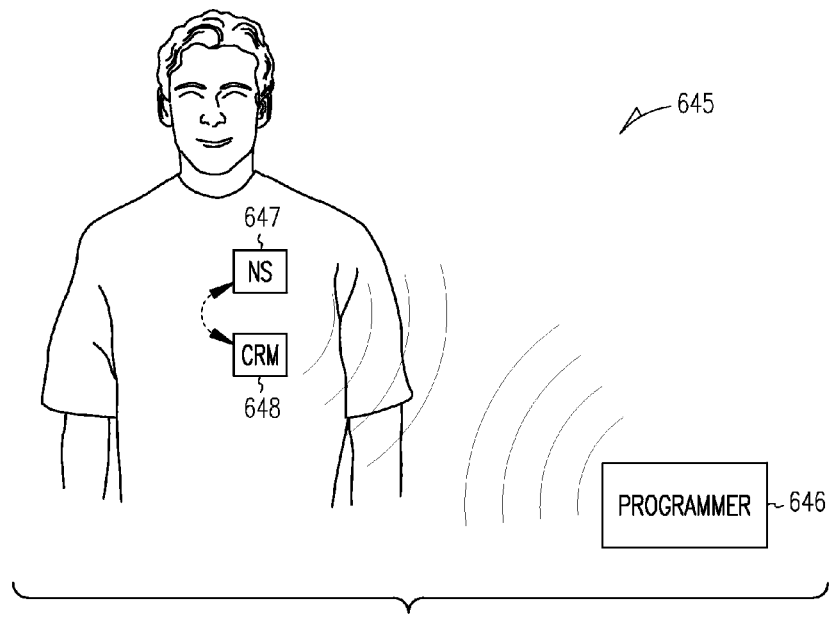
FIG. 6 illustrates a system including a programmer, an implantable neural stimulator (NS) device and an implantable cardiac rhythm management (CRM) device, according to various embodiments.

FIG. 6 illustrates a system 645 including a programmer 646, an implantable neural stimulator (NS) device 647 and an implantable cardiac rhythm management (CRM) device 648, according to various embodiments of the present subject matter. Various aspects involve a method for communicating between an NS device and a CRM device or other cardiac stimulator. This communication allows one of the devices 647 or 648 to deliver more appropriate therapy (i.e. more appropriate NS therapy or CRM therapy) based on data and/or communication signals received from the other device. Some embodiments provide on-demand communications. The illustrated NS device and the CRM device are capable of wirelessly communicating with each other, and the programmer is capable of wirelessly communicating with at least one of the NS and the CRM devices. For example, various embodiments use telemetry coils to wirelessly communicate data and instructions to each other. In other embodiments, communication of data and/or energy is by ultrasonic means. In some embodiments, a lead provides a hardwired communication path between the two devices. An example of a CRM device is illustrated in FIGS. 3 and 4.

Figure 7:
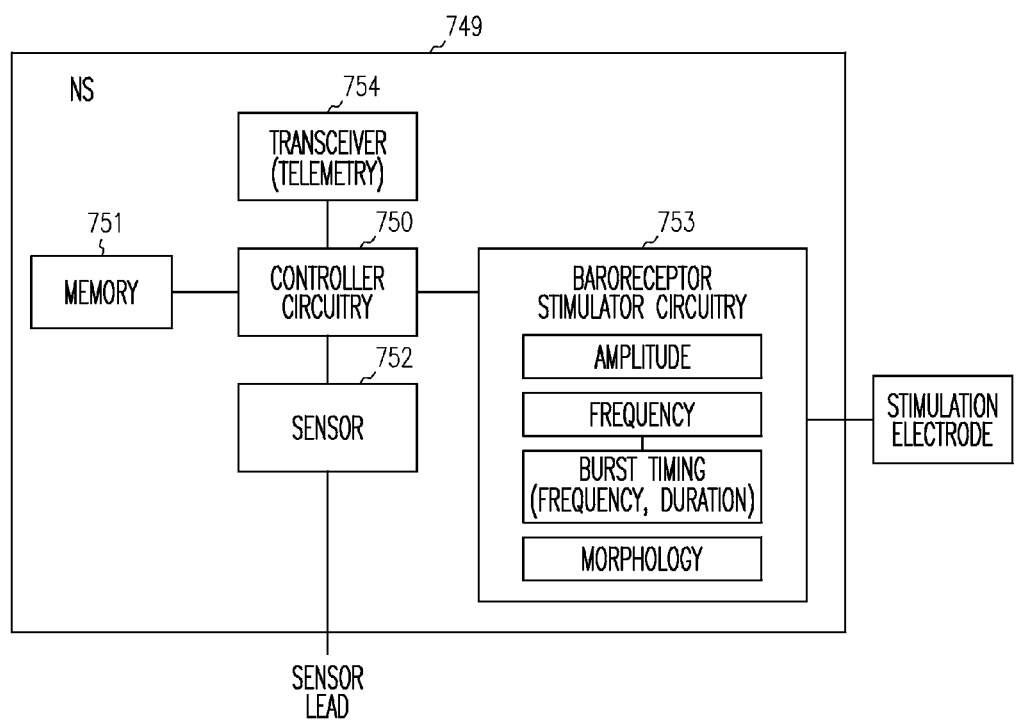
FIG. 7 illustrates an implantable neural stimulator (NS) device such as can be incorporated as the IMD in the system of FIG. 1 or as the neural stimulator in the system of FIG. 6, according to various embodiments of the present subject matter.

FIG. 7 illustrates an implantable neural stimulator (NS) device 749 such as can be incorporated as the IMD 101 in the system 100 of FIG. 1 or as the neural stimulator 647 in the system 645 of FIG. 6, according to various embodiments of the present subject matter. The illustrated neural stimulator 749 includes controller circuitry 750 connected to a memory 751, a sensor 752, a neural stimulation circuitry 753, and a transceiver 754. An electrode is connected to the stimulator circuitry 753. The memory includes instructions or algorithms operated on by the controller and further includes parameters for use in the algorithms to provide the desired neural stimulation therapy. Some embodiments use the sensor, such as a neural sensor or other physiologic sensor like a heart rate sensor, to provide feedback for the neural stimulation. The stimulator circuitry is adapted to adjust parameters of the neural stimulation signal transmitted to the electrode. According to various embodiments, one or more of the amplitude, the frequency, the morphology and the burst timing (frequency and duration of bursts) are capable of being adjusted. The parameters in the memory are organized into parameter sets to selectively change the neural stimulation, such as by adjusting one or more of the parameters for the neural stimulation signal, depending on whether another therapy type is present.

Figure 8:
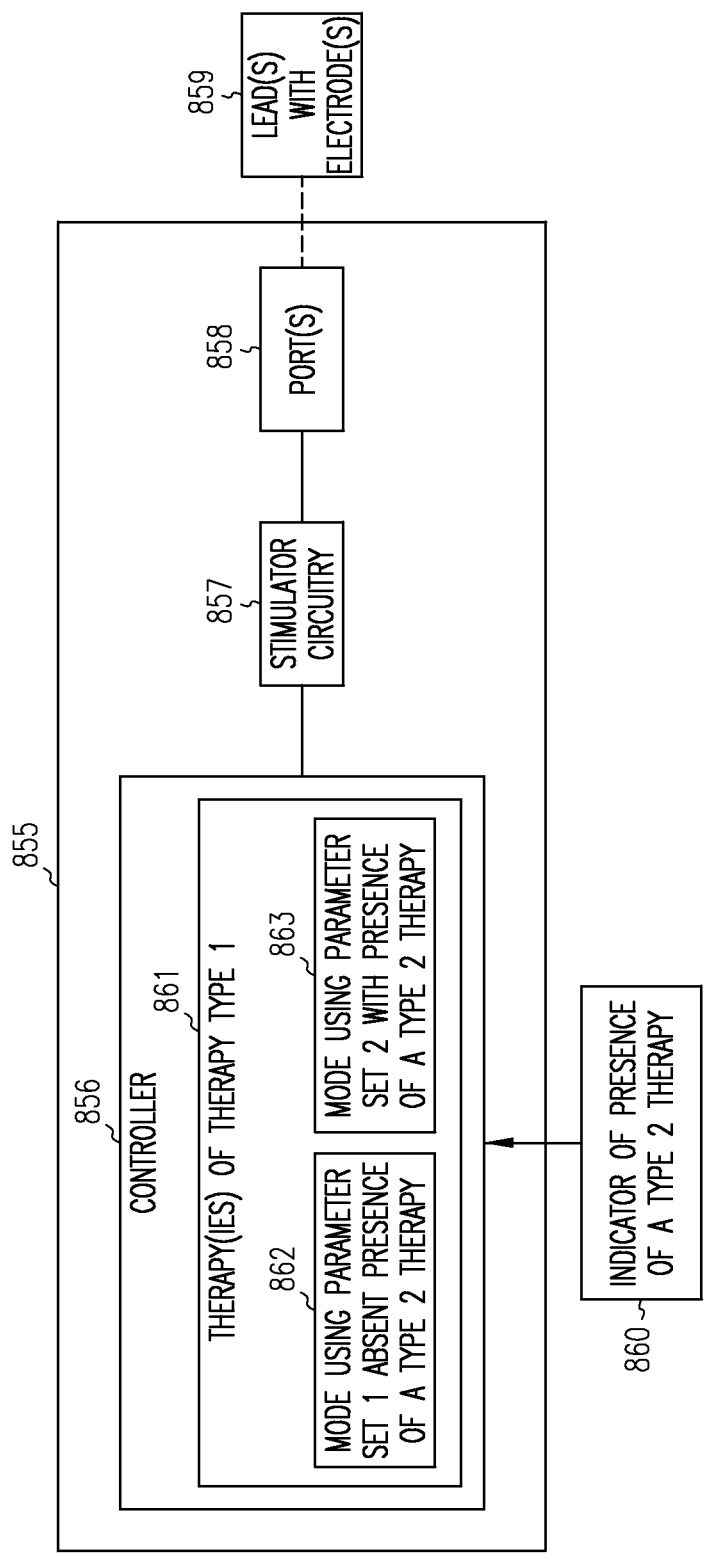
FIG. 8 illustrates a device, according to various embodiments, such as the IMD illustrated in FIG. 1, for example.

FIG. 8 illustrates a device, according to various embodiments of the present subject matter, such as the IMD illustrated in FIG. 1, for example. The illustrated device 855 is adapted to provide a first type of therapy, and includes a controller 856 connected to stimulator circuitry 857 to provide therapy. At least one port 858 is connected to the stimulator circuitry 857. The port(s) 858 are adapted to connect with at least one lead 859, with each lead including at least one electrode. The lead(s) and electrode(s) are positioned to provide a desired therapy. Each port provides a communication channel to an electrode.

The controller is adapted to receive an indicator of the presence of a second type of therapy 860. The controller is adapted to provide at least one therapy of the first therapy type 861, and is able to operate in two modes. The controller enters one therapy mode 862 which uses a first parameter set to provide the therapy of the first type when the second type of therapy is not present. The controller enters another therapy mode 863 which uses a second parameter set to provide the therapy of the first type when the second type of therapy is present. Thus, even if the therapy of the second type is intermittent in nature, the device is able to continue to deliver the first type of therapy.

Figure 9:
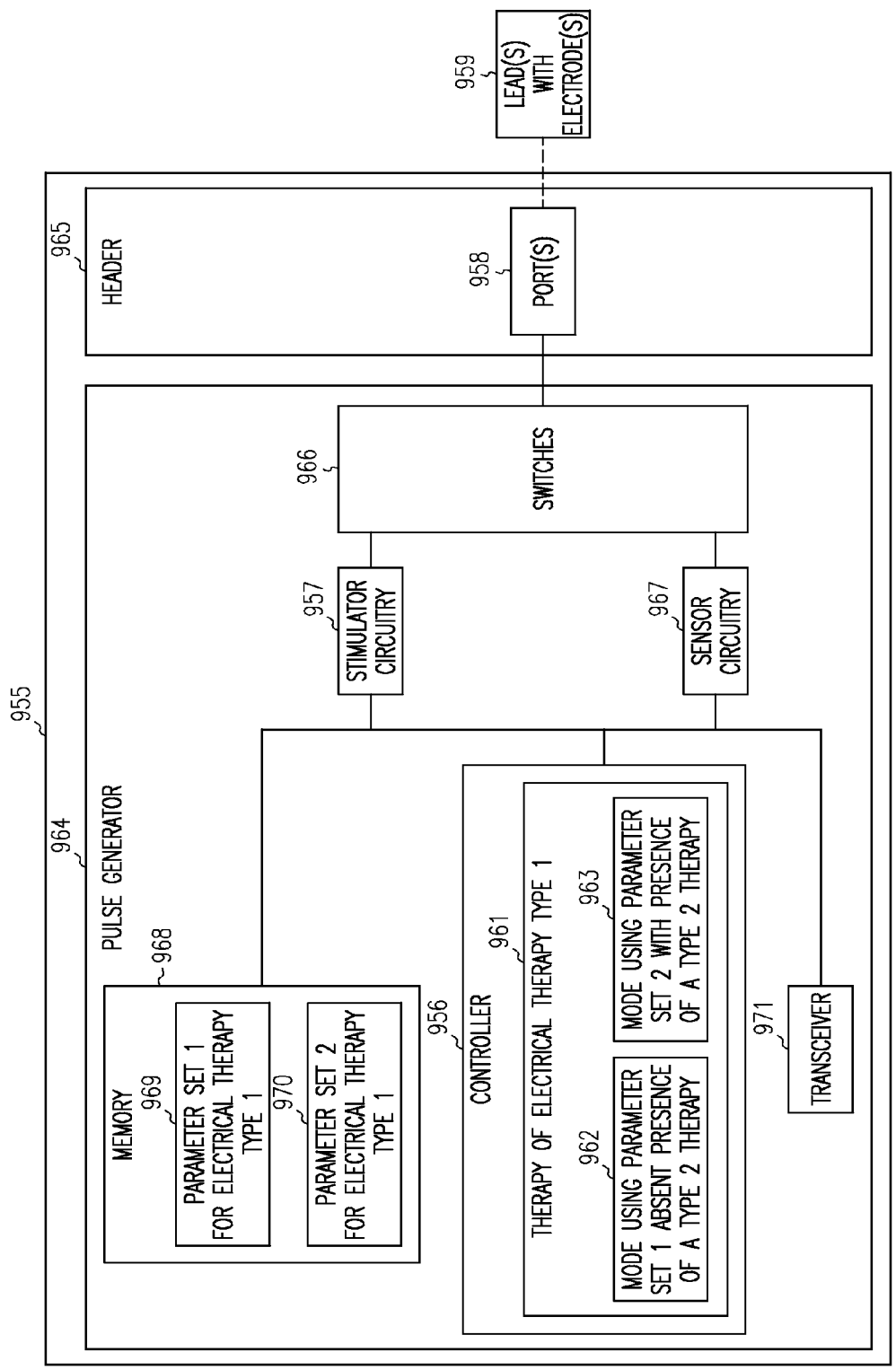
FIG. 9 illustrates a device, according to various embodiments, such as the IMD illustrated in FIG. 1, for example.

FIG. 9 illustrates a device, according to various embodiments of the present subject matter, such as the IMD illustrated in FIG. 1, for example. The illustrated device 955 includes a header section 965 and a pulse generator section 964. The pulse generator section includes the processing circuitry, and the header provides a physical interface to receive leads 959 and further provides electrical interfaces via ports to provide communication channels to each lead electrode.

The illustrated device 955 is adapted to provide a first type of therapy, and includes a controller 956 connected to stimulator circuitry 957 to provide therapy. At least one port 958 is connected to the stimulator circuitry 957 via switches 966. Sensor circuitry 967 is also connected to the at least one port 958 via the switches 966. The switches are used to allow the same communication channel to be used for both stimulation and sensing. The sensor circuitry 967 is connected to the controller 956.

The device 955 further includes memory 968, which includes instructions and a plurality of adjustable parameters to control the therapy. As illustrated, the parameters are organized into two parameter sets 969 and 970. The controller receives an indicator of the presence of a second type of therapy, such as a detected therapy via the sensor circuitry 967 and/or a communicated signal via transceiver 971. The controller is adapted to provide at least one therapy of the first therapy type 961, and is able to operate in two modes. The controller enters one therapy mode 962 which uses a first parameter set 969 to provide the therapy of the first type when the second type of therapy is not present. The controller enters another therapy mode 963 which uses a second parameter set 970 to provide the therapy of the first type when the second type of therapy is present.

The present subject matter is capable of automatically adjusting parameters used to deliver therapy of a first type in response to whether therapy of a second type is present. The present subject matter is also capable of automatically adjusting parameters used to deliver therapy of the first type based on the intensity of the therapy of the second type. Such embodiments can be based on one or more threshold intensities that define different intensity levels. Each intensity level can be associated with a parameter set. Some embodiments adjust the parameters proportionally to the intensity of the second therapy. The parameter adjustments can be linearly or nonlinearly related to the intensity change for the therapy of the second type. The parameter set used for the therapy of the first therapy type can be based solely on whether the therapy of the second therapy type is present, can be based solely on an intensity of the therapy of the second therapy type, and can be based on a combination of whether the therapy of the second therapy type is present and the intensity of the therapy of the second therapy type.

Figure 10:
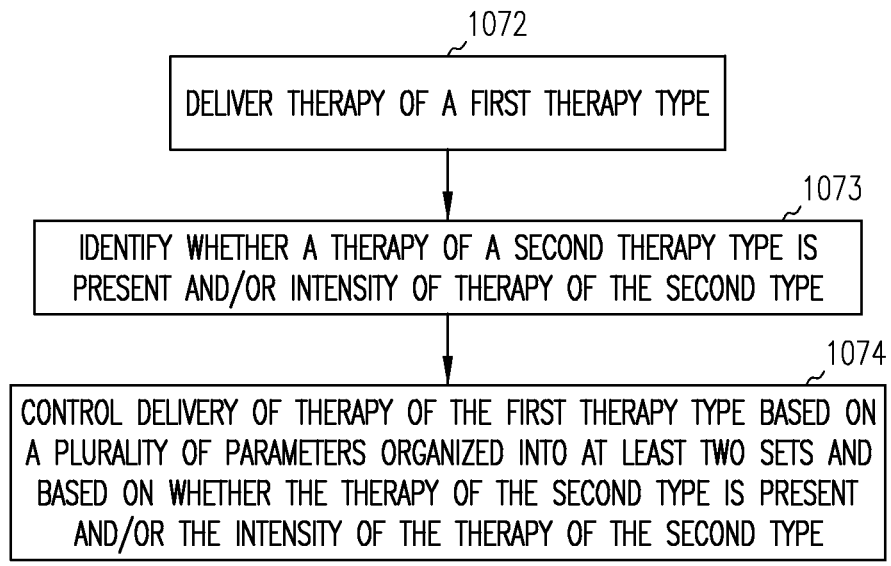
FIG. 10 illustrates a method, according to various embodiments.

FIG. 10 illustrates a method, according to various embodiments. At 1072, a therapy (e.g. bradycardia support pacing) of a first type (e.g. CRM therapy) is delivered. At 1073, it is determined whether a therapy (e.g. neural stimulation of cardiac fat pad) of a second therapy type (neural stimulation therapy) is present and/or the intensity of the therapy of the second type is determined. At 1074, the delivery of therapy of the first therapy type is controlled based on a plurality of parameters organized into at least two sets and based on whether the therapy of the second type is present and/or the intensity of the therapy of the second type.

Figure 11A:
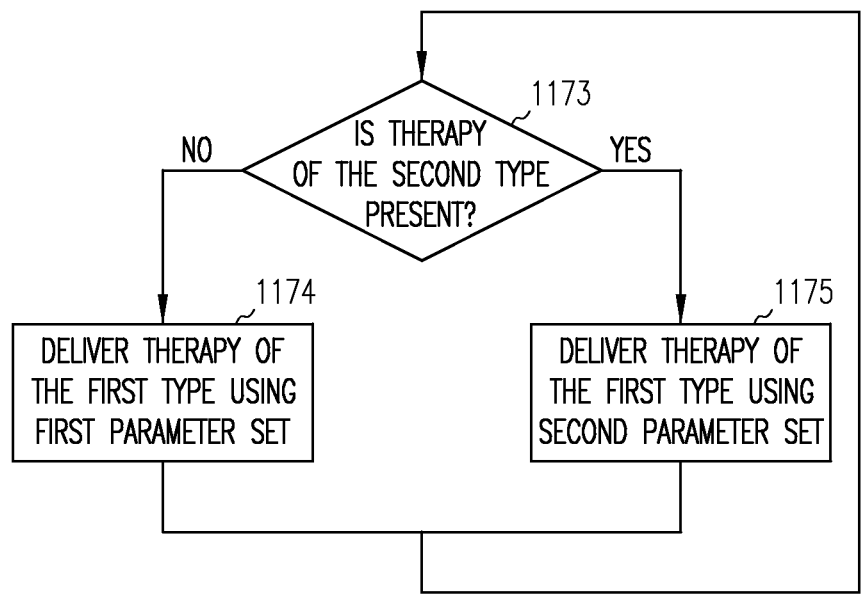
FIG. 11A illustrates a method for controlling delivery of therapy of the first type (e.g. CRM therapy) based on a plurality of parameters organized into at least two sets and based on whether the therapy of the second type (e.g. neural stimulation therapy) is present, according to various embodiments.

FIG. 11A illustrates a method for controlling delivery of therapy of the first type (e.g. CRM therapy) based on a plurality of parameters organized into at least two sets and based on whether the therapy of the second type (e.g. neural stimulation therapy) is present, according to various embodiments. At 1173, it is determined whether the therapy of the second type is present. If the second type of therapy is not present, the process proceeds to 1174 where the therapy of the first type is delivered using a first parameter set 1174. If the second type of therapy is present, the process proceeds to 1175 where the therapy of the first type is delivered using a second parameter set 1175.

Figure 11B:
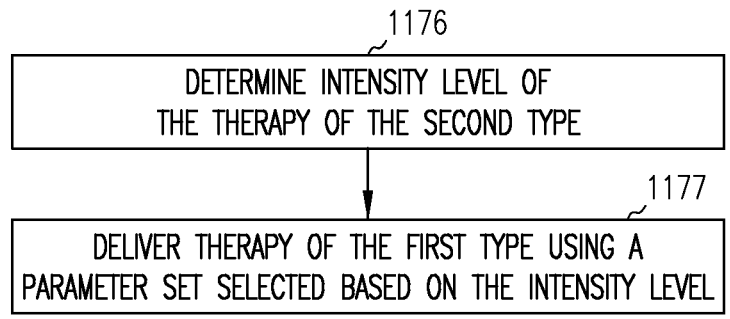
FIG. 11B illustrates a method for controlling delivery of therapy of the first type (e.g. CRM therapy) based the intensity of the therapy of the second type (e.g. neural stimulation therapy), according to various embodiments.

FIG. 11B illustrates a method for controlling delivery of therapy of the first type (e.g. CRM therapy) based the intensity of the therapy of the second type (e.g. neural stimulation therapy), according to various embodiments. At 1176, the intensity level of the therapy of the second type is determined. The determination of the intensity level can be use a few distinct levels separated by threshold values, such as a high and low intensity, or can more precisely quantify the intensity level throughout the continuum from the lowest to highest intensities. At 1177, therapy of the first type is delivered using a parameter set selected based on the intensity level determined at 1176.

Figure 11C:
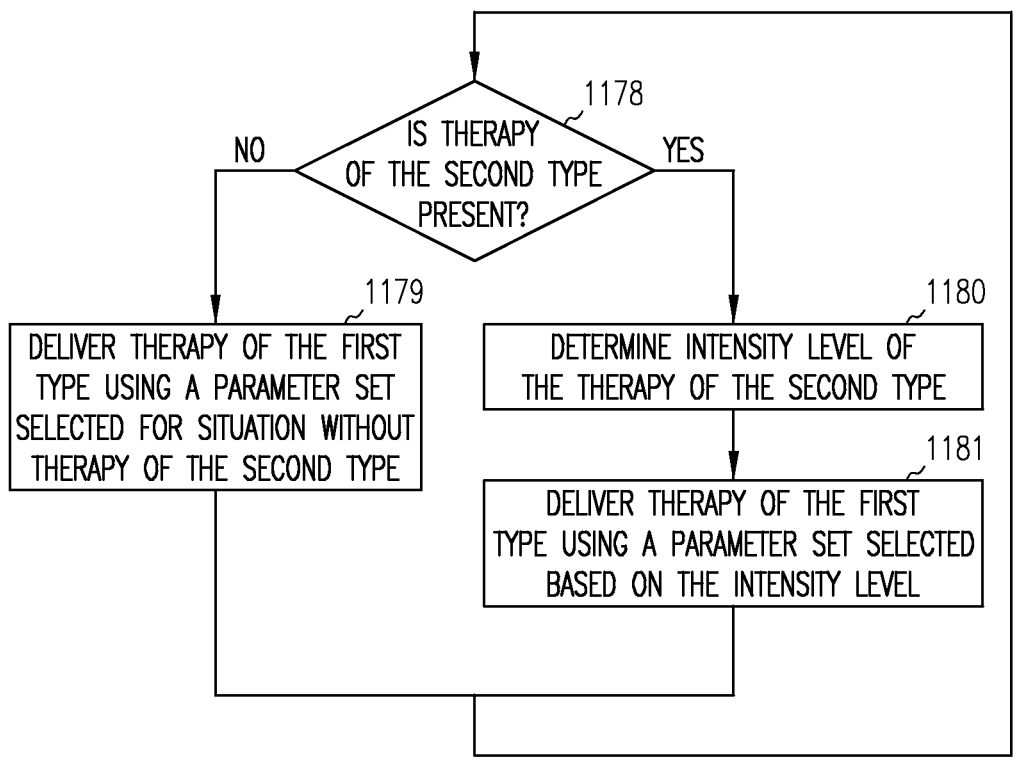
FIG. 11C illustrates a method for controlling delivery of therapy of the first type (e.g. CRM therapy) based on whether the therapy of the second type (e.g. neural stimulation therapy) is present and on the intensity of the therapy of the second type, according to various embodiments.

FIG. 11C illustrates a method for controlling delivery of therapy of the first type (e.g. CRM therapy) based on whether the therapy of the second type (e.g. neural stimulation therapy) is present and on the intensity of the therapy of the second type, according to various embodiments. At 1178, it is determined whether therapy of the second type is present. If the therapy of the second type is not present, the process proceeds to 1179, where therapy of the first type is delivered using a parameter set selected for situations without the therapy of the second type. If the therapy of the second type is present, the process proceeds to 1180 where the intensity level of the therapy of the second type is determined, and to 1181 where the therapy of the first types is delivered using a parameter set selected based on the intensity level.

Figure 12A:
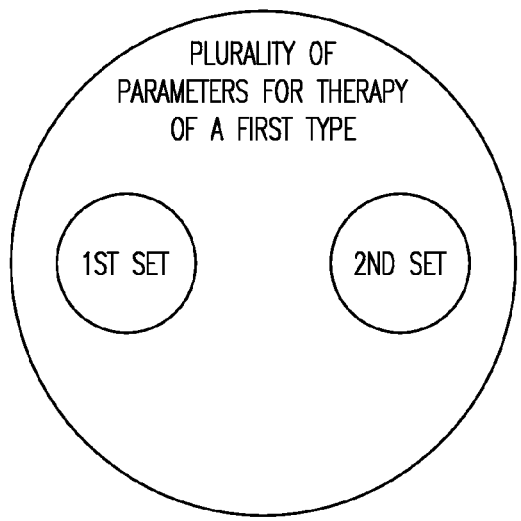
FIGS. 12A, 12B and 12C illustrate plurality of parameters, and further illustrate the first and second sets of parameters, according to various embodiments.
Figure 12B:
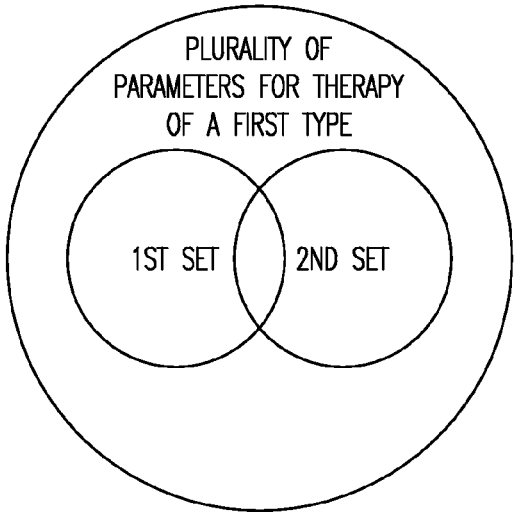
Figure 12C:
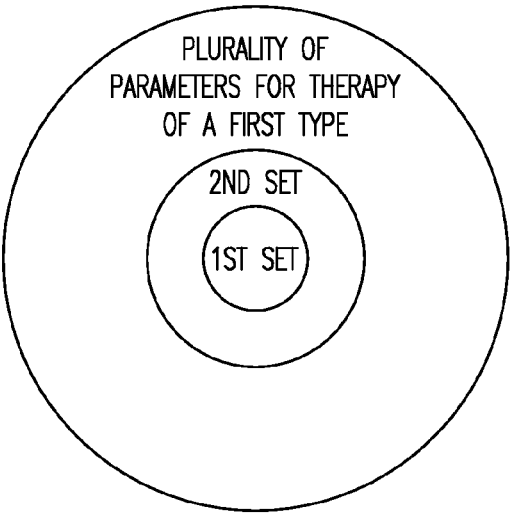

FIGS. 12A, 12B and 12C illustrate plurality of parameters, and further illustrate the first and second sets of parameters, according to various embodiments. FIG. 12A illustrates a first set and a second set in which the sets are exclusive of each other. That is, the sets are defined and organized to be mutually exclusive such that each set includes distinct parameters with respect to the other set. FIG. 12B illustrates a first set and a second set that are at least partially inclusive, being defined and organized to share at least some parameters. FIG. 12C illustrates a first set that is a subset of the second set. In addition to the illustrated relationships between the first and second sets, some embodiments may include sets with the same parameters, where the differences between the parameter sets are provided by different adjustable or programmable values of the parameters.

In some embodiments, all of the adjustable parameters in each parameter set are independently programmable. In some embodiments, the adjustable parameters in one parameter set is programmable, and the adjustable parameters in the other parameter set are automatically adjusted as a function of the values for the parameters in the first parameter set.

One of ordinary skill in the art will understand that, the modules and other circuitry shown and described herein can be implemented using software, hardware, and combinations of software and hardware. As such, the illustrated modules and circuitry are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. For example, various embodiments combine two or more of the illustrated processes. Two or more sensed parameters can be combined into a composite parameter used to provide a desired CRM therapy. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. A system to deliver an electrical therapy to a patient to whom another electrical therapy is also delivered, comprising:
an electrical stimulator to deliver electrical pulses to the patient for the electrical therapy; and
a controller connected to the electrical stimulator and configured to use a set of one or more stimulation parameters to control delivery of the electrical pulses for the electrical therapy before a change in the other electrical therapy, the controller configured to account for and be responsive to the change in the other electrical therapy in delivering the electrical therapy to the patient by using another set of one or more stimulation parameters.

2. The system of claim 1, wherein the controller is configured to receive a communication alerting the controller about delivery of the other electrical therapy to the patient.

3. The system of claim 1, further comprising at least one physiological sensor connected to the controller, wherein the controller is configured to receive feedback from the at least one physiological sensor and use the feedback to control delivery of the electrical pulses for the electrical therapy.

4. The system of claim 1, wherein the controller is configured to account for a change in a presence of the other electrical therapy.

5. The system of claim 1, wherein the controller is configured to account for a change in an intensity of the other electrical therapy.

6. The system of claim 1, wherein the controller is configured to account for both a change in a presence and a change in an intensity of the other electrical therapy.

7. The system of claim 1, wherein the electrical therapy includes a neural stimulation therapy, and the other electrical therapy includes a ventricular defibrillation therapy.

8. The system of claim 1, wherein the electrical therapy includes a neural stimulation therapy, and the other electrical therapy includes an atrial defibrillation therapy.

9. The system of claim 1, wherein the electrical therapy includes a neural stimulation therapy, and the other electrical therapy includes a bradycardia pacing therapy.

10. The system of claim 1, wherein the electrical therapy includes a neural stimulation therapy, and the other electrical therapy includes a tachycardia pacing therapy.

11. The system of claim 1, wherein the electrical therapy includes a neural stimulation therapy, and the other electrical therapy includes a pacing therapy, the pacing therapy having a pacing mode, the pacing mode including an atrial pacing mode or a ventricular pacing mode or a dual chamber pacing mode.

12. The system of claim 1, wherein the other electrical therapy is an intermittent electrical therapy.

13. The system of claim 1, wherein the electrical stimulator and the controller are housed within an implantable housing of an implantable medical device, and wherein the other electrical therapy is delivered to the patient by another device.

14. The system of claim 13, wherein the other device is another implantable medical device.

15. A system to deliver an electrical neural stimulation therapy to a patient to whom another electrical therapy is delivered to myocardia of the patient, comprising:
an electrical stimulator to deliver electrical pulses to the patient for the electrical neural stimulation therapy; and
a controller connected to the electrical stimulator and configured to use a set of one or more stimulation parameters to control delivery of the electrical pulses for the electrical neural stimulation therapy before a change in the other electrical therapy, the controller configured to receive a communication alerting the controller about delivery of the other electrical therapy to the patient, the controller configured to account for and be responsive to the change in the other electrical therapy to the myocardia in delivering the electrical neural stimulation therapy to the patient by using another set of one or more stimulation parameters, at least one of the sets including at least one different stimulation parameter or at least one different parameter value.

16. The system of claim 15, wherein the controller is configured to account for a change in a presence of the other electrical therapy, or is configured to account for a change in an intensity of the other electrical therapy, or is configured to account for both a change in a presence and a change in an intensity of the other electrical therapy.

17. The system of claim 15, wherein the other electrical therapy to the myocardia includes a ventricular defibrillation therapy or an atrial defibrillation therapy, a bradycardia pacing therapy, or a tachycardia pacing therapy.

18. The system of claim 15, wherein the other electrical therapy to the myocardia includes a pacing therapy, the pacing therapy having a pacing mode, the pacing mode including an atrial pacing mode or a ventricular pacing mode or a dual chamber pacing mode.

19. A system to deliver an electrical therapy and another electrical therapy to a patient, comprising:
a first implantable medical device configured to deliver the electrical therapy to the patient;
a second device configured to intermittently deliver the other electrical therapy to the patient;
the first implantable medical device including:
an electrical stimulator to deliver electrical pulses to the patient for the electrical therapy; and
a controller connected to the electrical stimulator and configured to use a set of one or more stimulation parameters to control delivery of the electrical pulses for the electrical therapy before a change in the other electrical therapy, the controller configured to account for and be responsive to the change in the other electrical therapy in delivering the electrical therapy to the patient by using another set of one or more stimulation parameters, at least one of the sets including at least one different stimulation parameter or at least one different parameter value.

20. The system of claim 19, wherein the second device is configured to send an alert concerning delivery of the other electrical therapy, the controller is configured to receive the alert and account for the other therapy in response to the alert.

* * * * *